(12) United States Patent
Webler, Jr. et al.

(10) Patent No.: US 9,656,030 B1
(45) Date of Patent: May 23, 2017

(54) SYSTEM FOR THE INJECTION OF CELLS AND/OR BIOLOGICALLY ACTIVE MATERIALS INTO CORONARY ARTERIES FOR THERAPEUTIC PURPOSES

(71) Applicant: Abbott Cardiovascular Systems Inc., Santa Clara, CA (US)

(72) Inventors: William Earl Webler, Jr., San Jose, CA (US); Eugene T. Michal, San Francisco, CA (US); Jessica Chiu, Belmont, CA (US); Charles D. Claude, San Jose, CA (US); Syed Faiyaz Ahmed Hossainy, Fremont, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 284 days.

(21) Appl. No.: 13/844,222

(22) Filed: Mar. 15, 2013

(51) Int. Cl.
  *A61M 5/48* (2006.01)
  *A61M 25/10* (2013.01)

(52) U.S. Cl.
  CPC ............ *A61M 5/482* (2013.01); *A61M 5/484* (2013.01); *A61M 25/10* (2013.01)

(58) Field of Classification Search
  CPC ........ A61M 5/484; A61M 5/482; A61M 5/48; A61M 5/488; A61M 5/142; A61M 2025/1052; A61M 25/10; A61M 25/1002
  USPC ....... 604/503, 508, 509, 510, 523, 528, 532, 604/96.01, 101.04, 103.01, 97.01, 97.02, 604/99.01; 600/486; 606/200
  See application file for complete search history.

(56) References Cited

U.S. PATENT DOCUMENTS

| | | | |
|---|---|---|---|
| 7,211,073 B2* | 5/2007 | Fitzgerald et al. | 604/500 |
| 2003/0073953 A1* | 4/2003 | Mische | A61B 17/22012 604/152 |
| 2004/0208823 A1* | 10/2004 | Carpenter, Jr. | 424/1.49 |

(Continued)

OTHER PUBLICATIONS

Denise Macklin ("Infusion Pump Therapy A Guide for Clinicians and Educators", https://www.hospira.com/en/images/P11_3241_Infusion_Pump_Therapy_Pocket_Guide_FINAL_tcm81-90336.pdf, Apr. 2011).*

(Continued)

*Primary Examiner* — Christopher Cook
*Assistant Examiner* — Carolyn Pehlke
(74) *Attorney, Agent, or Firm* — Randy Shen; Blakely, Sokoloff, Taylor & Zafman LLP

(57) ABSTRACT

A method including percutaneously positioning a delivery device in a blood vessel; locally introducing a treatment agent from the delivery device into the blood vessel upstream of an infarcted area or distressed area; and following introducing the treatment agent, occluding the blood vessel for a dwell time sufficient to allow the treatment agent to flow into targeted capillaries in or adjacent to the infarcted area. A system comprising a delivery device suitable for percutaneous insertion into a blood vessel of a patient, the delivery device comprising an occluding portion and a delivery cannula having a lumen therethrough; a controller coupled to a proximal portion of the delivery device comprising instruction logic to perform a method including introducing a treatment agent into the delivery cannula; and occluding a blood vessel following a predetermined delay time after introducing the treatment agent.

15 Claims, 11 Drawing Sheets

(56) References Cited

U.S. PATENT DOCUMENTS

| | | | |
|---|---|---|---|
| 2005/0015048 A1* | 1/2005 | Chiu | A61M 25/10 604/101.04 |
| 2008/0200377 A1* | 8/2008 | Trollsas et al. | 514/12 |
| 2008/0300573 A1* | 12/2008 | Consigny et al. | 604/509 |
| 2010/0168649 A1* | 7/2010 | Schwartz | A61B 5/0215 604/22 |
| 2014/0003687 A1* | 1/2014 | Jou | A61B 6/481 382/130 |

OTHER PUBLICATIONS

Ben Best ("Electrocardiogram (ECG, EKG) Interpretation", http://www.benbest.com/health/ECG.html, Dec. 2009).*

Bae, Kyongtae T. "Intravenous contrast medium administration and scan timing at CT: considerations and approaches 1." Radiology 256.1 (2010): 32-61.*

* cited by examiner

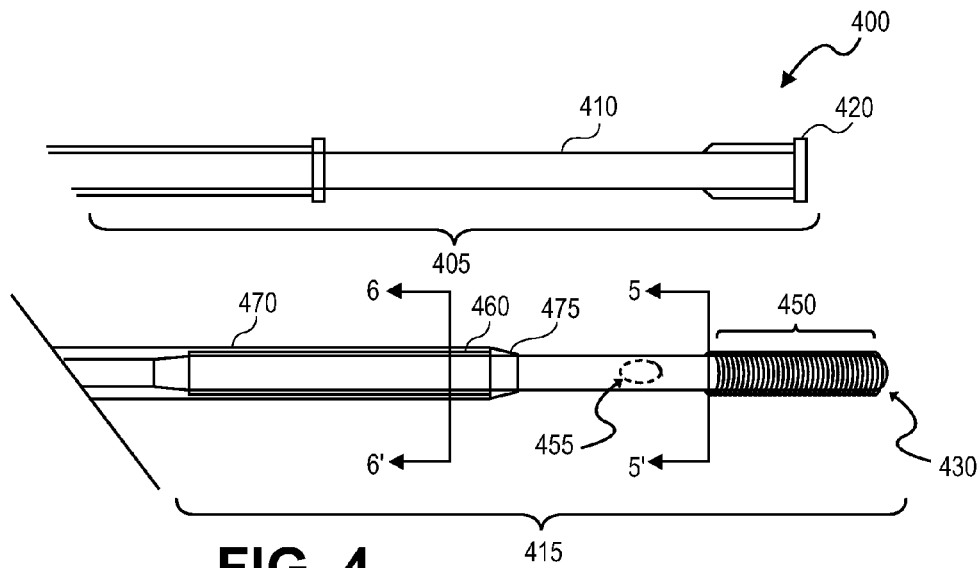
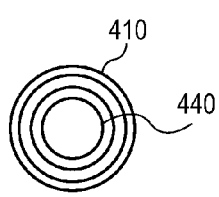
FIG. 5
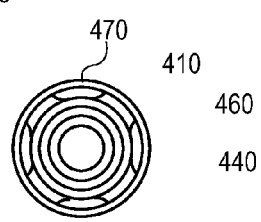
FIG. 6
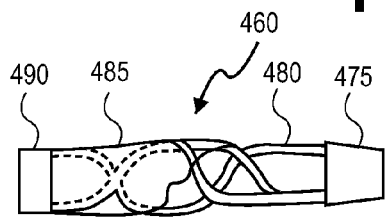
FIG. 7
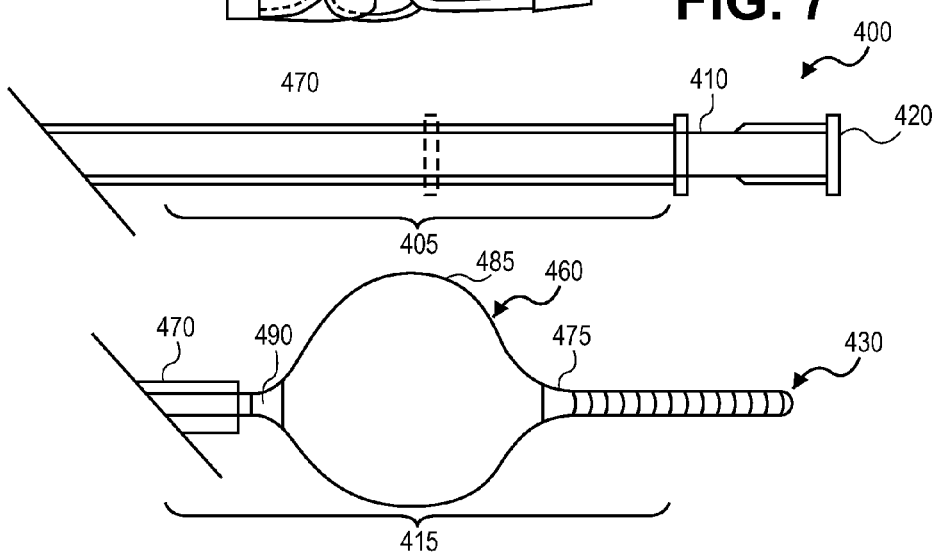
FIG. 8

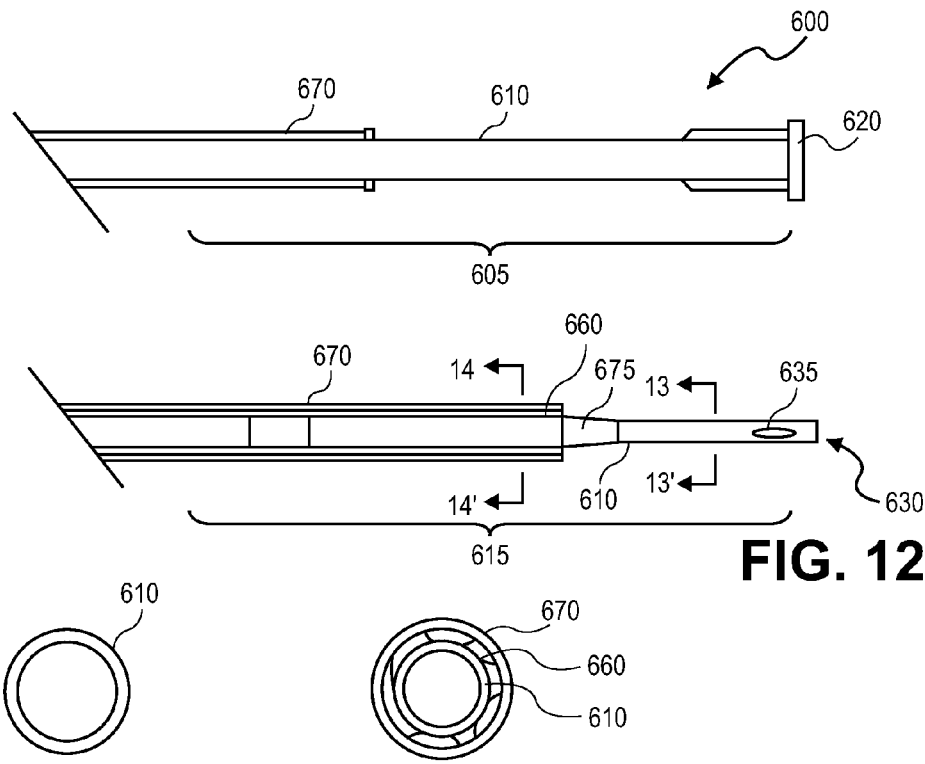
FIG. 12
FIG. 13   FIG. 14
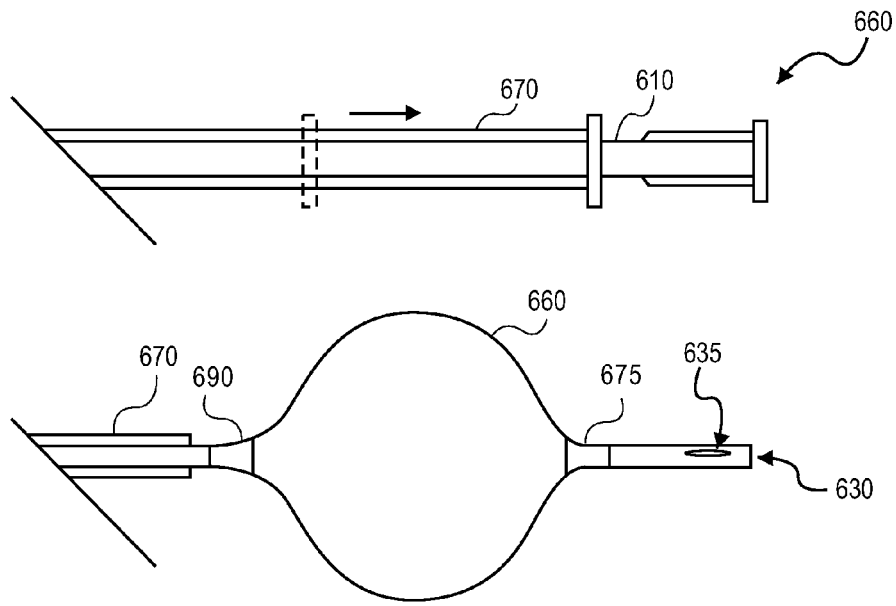
FIG. 15

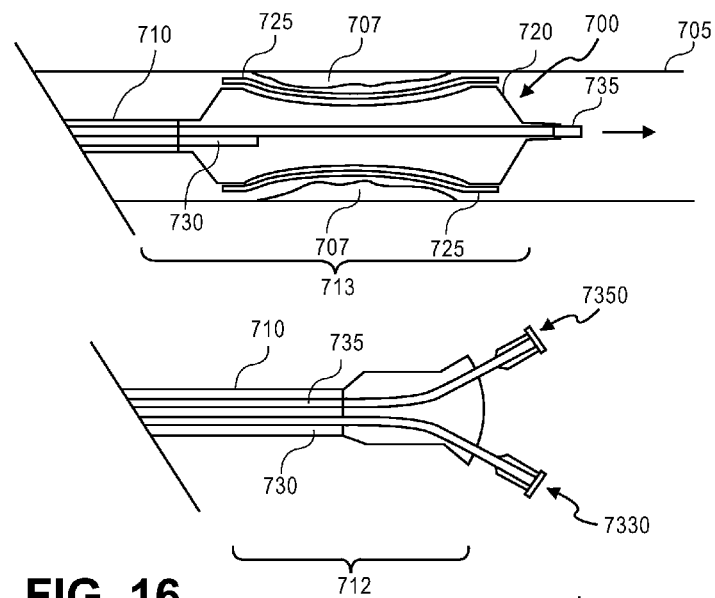
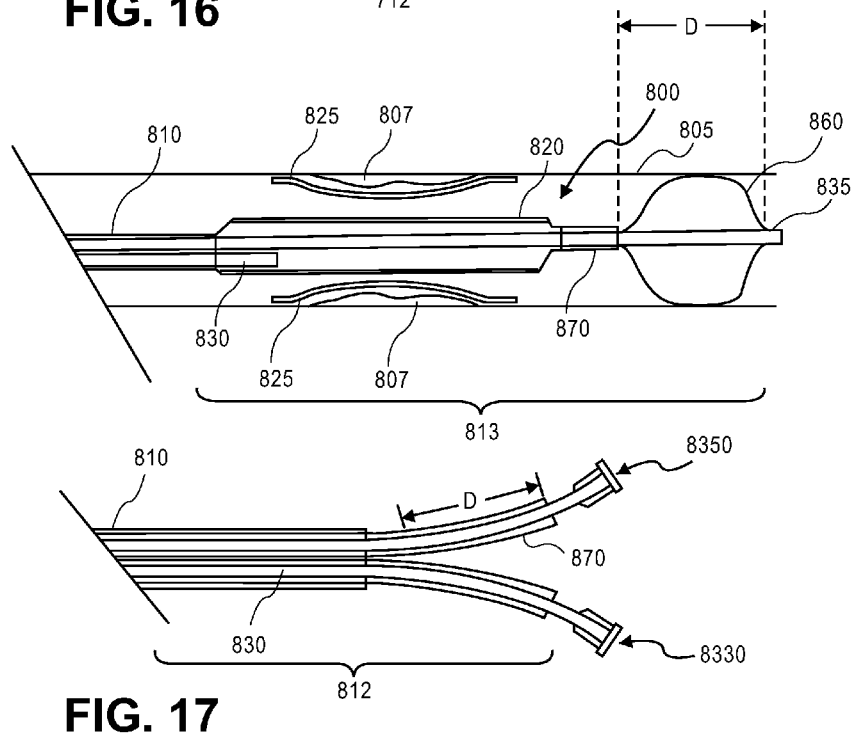
FIG. 16
FIG. 17

SYSTEM FOR THE INJECTION OF CELLS AND/OR BIOLOGICALLY ACTIVE MATERIALS INTO CORONARY ARTERIES FOR THERAPEUTIC PURPOSES

BACKGROUND

Field

Percutaneous transluminal therapy.

Background

Recent studies utilizing autologous mononuclear cells obtained from blood or bone marrow indicate that the introduction (e.g., injection) of these cells into coronary blood vessels (e.g., coronary arteries) will provide a therapeutic benefit to recently infarcted cardiac muscles/vessels as demonstrated by improved cardiac function. In these studies, the injection of a predetermined volume (fluid) of suspended cells is performed via a balloon catheter with an over-sized balloon inflated at a low pressure to avoid additional vessel damage that can lead to stenoses/occlusion. The inflation of the balloon is intended to block coronary blood flow during and for a relatively long period (e.g., about three minutes) after the injection. Following the dwell time, the balloon is deflated for at least a similar time to prevent additional ischemic damage. This procedure is repeated until a desired volume/number of cells has been injected. It is also likely that this procedure may be of benefit to patients suffering from Chronic Heart Failure (CHF).

In the above-described procedure, the coronary blood flow is interrupted to increase the dwell time of the cells in the capillaries and/or the infarcted tissue region. As has been shown by CT and MRI delayed contrast enhancement techniques, infarcted tissue regions contain at least some disrupted/leaky microvasculature that may allow the infused cells to contact tissue in the infarcted region without passing through a capillary wall. Typically, the more time that the cells are in the capillaries and/or the infarcted tissue region, the more opportunities the cells have to adhere to the capillary walls and/or adjacent tissues and transmigrate (travel) into the adjacent tissue where they may multiply and differentiate into tissue types that repair damaged tissues and/or may secrete chemicals that preserve the still living portions of infarcted tissue regions. Transmigration only occurs to a significant extent in the capillaries feeding infarcted or distress tissue regions and in the infarcted or distressed tissue regions. It is believed that the ischemic, distressed and recently infarcted (dead) tissue produces/releases chemicals that signal at least some portion of the mononuclear cells in their vicinity to transmigrate toward/to their location. It is believed that the transmigrated cells differentiate and create new vascular tissue and/or secrete chemicals that preserve the still living tissues (prevent apoptosis) and encourage tissue growth/repair in an infarcted or distressed tissue region.

The above described procedure of introducing mononuclear cells to provide a therapeutic benefit to recently infarcted, ischemic and/or distressed cardiac muscles/vessels is inefficient in at least two ways. First, only a portion of the cells injected can be resident in the capillaries during the occlusion of the arteries. This occurs because the injected suspension of cells must displace most of the blood and fill the volume of the arteries and arterioles distal to the occluding balloon and proximal of the infarcted or distressed region's microvasculature. The cells in this volume will not have the extended time to transmigrate, as they will be washed through the infarcted region once the vessel occlusion is removed by the blood flow.

The second inefficiency is a result of the vascular response to occlusion. Not all of the tissues fed (provided blood) by a recently occluded and now open artery (the one that caused the infarction) will be ischemic, dead, or irreversibly damaged. This is because some of the tissue contains capillaries that are fed by different coronary arteries or by artery branches proximal of the recent occlusion and these capillaries keep the tissue (vessels and muscles) alive, but often in a stunned condition until the occluded site is reopened. It is known that the flow through recently infarcted tissue is abnormal, such that materials injected into their feeding artery will remain resident in infarcted tissues longer (i.e., will wash out slower). This is thought to be a result of the disrupted vessels in the infarcted tissue (the vessel wall cells of the capillaries themselves are dead or damaged and allow leakage directly into the surrounding interstitial spaces). It is also good evidence that the vessel flow resistance of infarcted tissue regions is higher than that of normal tissues. The higher the local flow resistance, the lower the local flow rate and the more time it takes to wash a material into and out from the local tissues and vessels. Also, it is known that as normal tissues become ischemic, their local arterioles become dilated, lowering the local flow resistance and increasing the blood flow through the local tissue (capillaries). Coronary flow reserve (CFR) testing performed at recently occluded sites feeding infarcted tissue regions demonstrates the capacity of at least some of the arterioles to dilate/increase regional blood flow and is good evidence that a recently occluded artery (e.g. by a coronary thrombosis) is feeding at least some normally functioning vasculature and cardiac muscle tissues that can respond to ischemia in the normal way.

Occluding a vessel at a low pressure with a balloon takes a relatively long time. If an inflation fluid is injected at a high pressure to make the inflation more rapid, a potential risk develops of applying a high pressure or oversized balloon to the artery and damaging the artery wall, leading to a restenosis. Efforts to address these problems include making an inflation lumen (and thus the catheter) larger in cross-section (outside diameter (OD)) and/or shorter in length. Larger OD catheters are typically more difficult to position, obstruct blood flow more and lead to more severe insertion site complications. Short catheters restrict the insertion site choices to those not commonly used in a catheter laboratory environment. Attempts to achieve a rapid controlled volume injection require a very compliant and/or over-sized balloon and/or knowledge of the size of the artery and balloon/catheter volume along with specialized injection devices and procedures to avoid vessel injuries. Such balloons, devices and systems are under development but they may be difficult to rapidly deploy and/or control effectively and/or have ease of use issues in the field. As such, currently, the blood flow in an artery will be reduced or occluded for a period of time during the balloon inflation, any testing of the balloon occlusion effectiveness, and the time it takes the physician to lock the inflation in place and to perform the injection. Thus, the normal/more healthy tissues fed by the artery will be, at least to some degree, ischemic and have a lowered flow resistance. This has the effect of routing a greater percentage of a treatment agent (e.g., a cell suspension) flow to the normal/more healthy tissues and not to the distressed/damaged/dead tissues as desired. Additionally, after the injection and the relatively long time of occlusion are completed, the treatment agent resident in the vasculature proximal of the arterioles will be washed by the renewed blood flow through the capillaries. Thus, the treatment agent resident in the vasculature proximal of the arterioles will not only not have the benefit of the occlusion induced longer residence time in the capillaries but, due to that occlusion/ischemic time, will be preferentially routed by the arterioles through the capillaries of the most healthy tissues.

SUMMARY OF THE INVENTION

In one embodiment, the invention relates to a method of introducing a treatment agent such as a drug and/or a cellular component (e.g., bone marrow cells, potentially autologous mononuclear cells (stem cells, white blood cells, mesenchymal cells, and the like)) into a blood vessel such as a coronary artery to benefit an infarcted area. In one aspect, a method includes percutaneously positioning a delivery device in a blood vessel and locally introducing a treatment agent into the blood vessel upstream of an infarcted or distressed area (in the example of an artery). Following the introduction of a treatment agent, the blood vessel may not be occluded for a dwell time sufficient to allow the treatment agent to flow into targeted capillaries in or adjacent to the infarcted or distressed area. Recognizing that the blood vessel where the treatment agent may be introduced may feed arteries and arterioles associated with otherwise healthy tissues as well as infarcted or distressed tissues, the method includes introducing the treatment agent at a rate sufficient to substantially displace the blood flow in the vessel and/or in an amount sufficient to fill the targeted capillaries and under a condition that minimizes an increase in ischemia of the relatively healthy tissues fed by functioning arterioles and capillaries distal to the introduction point. Following introduction, the blood vessel may be occluded such that most of the treatment agent is washed into the capillaries when the flow in the vessel is minimized. In this manner, a greater portion of treatment agent will be resident in the desired capillaries during the occlusion and ischemia of relatively healthy tissues would not have started until the treatment agent is already in the desired capillaries.

In order to minimize ischemia of relatively healthy tissues fed by the blood vessel to be occluded, an embodiment of the invention contemplates the use of a delivery device that includes an occlusion device that may be rapidly deployed to occlude the blood vessel and de-deployed to resume blood flow. In one embodiment, the occlusion device may be expanded without inflating. An example of such a device is an expandable cage (e.g., a covered cage) that is connected to the exterior of the delivery device. In one embodiment, the expandable cage may be restrained in a collapsed configuration by a restraining sheath over the occluding device. Exposing the occlusion device by retracting the sheath allows the cage to expand to occlude a blood vessel.

In another embodiment of the invention, a system is described that controls the delivery of a treatment agent and the occlusion of a blood vessel according to parameters determined by the system or provided to the system.

In another embodiment, a method includes simultaneously or sequentially treating a target lesion in a blood vessel as well as an infarcted or distressed area downstream of the lesion. Methods include treating the target lesion through a stenting procedure (including, for example, with a drug eluting stent) and then using a lumen of the stent delivery device to delivery a treatment agent downstream from the lesion. Alternatively, multiple devices may be used, such as a device to treat the stent introduced in an artery (e.g., coronary artery) in a direction of blood flow and a device to treat the infarcted area introduced through a vein with the treatment agent introduced in a retrograde (opposite blood flow) fashion.

BRIEF DESCRIPTION OF THE DRAWINGS

Features, aspects, and advantages of embodiments will become more thoroughly apparent from the following detailed description, appended claims, and accompanying drawings in which:

FIG. 4 shows an embodiment of a delivery device of a hollow tube guidewire having an occlusion device thereon.

FIG. 5 shows the delivery device of FIG. 4 through line 5-5'.

FIG. 6 shows the delivery device of FIG. 5 through line 6-6'.

FIG. 7 shows a side view of the occlusion device of FIG. 4 in a retracted position.

FIG. 8 shows the delivery device of FIG. 4 wherein the occlusion device is in an expanded condition.

FIG. 12 shows a schematic side view of delivery device of a single lumen catheter having an occlusion device thereon with the occlusion device in a retracted position.

FIG. 13 shows the device of FIG. 12 through line 13-13'.

FIG. 14 shows the device of FIG. 12 through line 14-14'.

FIG. 15 shows a schematic side view of the device of FIG. 12 with the occlusion device in an expanded condition.

FIG. 16 shows a schematic side view of a delivery device within a blood vessel deploying a stent and capable of releasing a treatment agent.

FIG. 17 shows a cross-sectional side view of another embodiment of a delivery device in a blood vessel deploying a stent and capable of releasing of a treatment agent.

DETAILED DESCRIPTION

In one embodiment, a method is described. The method may be directed at benefiting infarcted tissue through a percutaneous intravenous technique. In one aspect, the invention relates to the percutaneous introduction of a treatment agent into coronary blood vessels, such as coronary arteries and veins. It is appreciated that the discussion herein is not limited to coronary tissues or introducing treatment agents into coronary vessels. Much of the treatment agent discussion that follows is directed at cellular components such as autologous or allogenic mononuclear cells including, but not limited to, embryonic stem cells, adult mesenchymal stem cells, bone marrow derived cells, adipose tissue derived cells and blood derived cells. The treatment agent may also include, either with a cellular component or without a cellular component, drugs, anti-inflammatory agents, anti-proliferative agents and other agents that may benefit an infarcted or distressed area. Examples of suitable drugs include everolimus, statins, oxidant signal antagonists (AGI-1067 available from Artherogenics, Inc. of Atlanta, Ga.) or other anti-inflammatories, eNOS regulators (e.g., available from Aventis Pharma of Frankfurt, Germany), tissue inhibitors of matrix metalloproteinases (TIMMPS), etc. In one sense, a treatment agent is an agent that will benefit the infarcted or distressed area (e.g., tissue) by itself creating new tissue cells and/or components thereof or trigger a repair or preservative mechanism. A treatment agent may also include an agent that may benefit an infarcted or distressed area (e.g., tissue) only with the assistance of another exogenous or endogenous agent.

In another embodiment, the treatment agent may be a solution or suspension of a cellular component, small molecule, peptide, protein, gene, or drug in microparticles or liposomes. Suitable biocompatible and biodegradable polymers form microparticles and/or nanoparticles include, but are not limited to, poly(lactic-co-glycolic acid) (PLGA) and poly(ester) amide (PEA).

Figure 1:
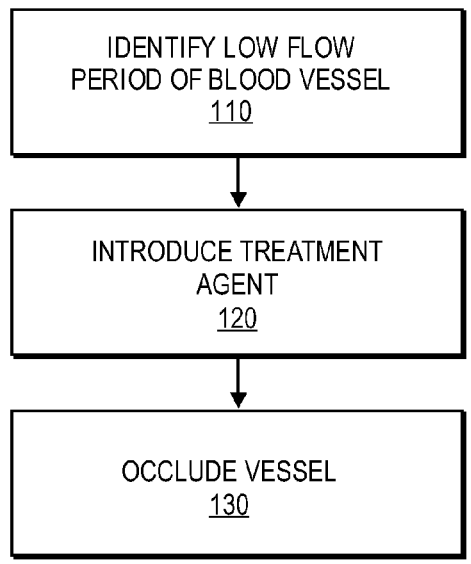
FIG. 1 shows a flow chart of an embodiment of a method for delivering a treatment agent.

FIG. 1 presents a flow chart of an embodiment of a method. The method includes identifying a low flow period of a blood vessel (block 110), introducing a treatment agent (block 120), and occluding the blood vessel (block 130). The method of FIG. 1 and its subsequent description tends to work well for the case when the entire injection is made during the time of low flow, which is within a portion of the cardiac cycle, and which is a relatively short time. This is sufficient when only a small volume of material is injected and/or the catheter infusion lumen is big enough to disperse the outflow downstream safely enough to inject the larger volume rapidly. However, there will be situations where this is not practical and the infusion instead will be during times of high flow also or over several cardiac cycles. Therefore, one method is to introduce the treatment agent at a volumetric rate sufficient to substantially replace the blood flow in the vessel which may help to avoid substantially diluting the treatment agent with blood. An average infusion rate as high as about 2 to 3 cc/sec may be appropriate in the coronaries (under rest/slightly sedated conditions) to sufficiently approximately match the existing flow rate in the coronary. If your infusion rate is too high, then at significant treatment agent volumes, the treatment agent may tend to flow substantially retrograde in the artery and may tend to flow into other vessel branches and/or (in the case of the coronaries) out of the coronaries and into the aorta. If your infusion rate is too low, then the treatment agent may tend to be substantially diluted by the blood and/or a situation may be created where, with the volume of treatment agent to be injected, many infusion-occlusion cycles may be needed or an undesirably large portion of the treatment agent may not be resident in the target capillaries during the occlusion. There are advantages to beginning the infusion of the treatment agent at the start of and/or during the low flow time of the artery, since this tends to provide the greatest concentration of the treatment agent (e.g., due to least blood dilution) at the front of the treatment agent bolus in the artery. This also tends to reduce the volume of the treatment bolus (e.g., volume of treatment agent and treatment agent mixed with blood). Moreover, if the infusion can be completed during the low flow time, the entire treatment bolus may have high concentration in a small volume. The normal low flow time of the coronary arteries is during systole and the low flow time of the systemic arteries is during diastole (lower aortic/systemic blood pressures). A small volume treatment bolus tends to be easier to stop in the target capillaries with an occlusion than a larger volume treatment bolus. If the treatment bolus volume exceeds the volume of the capillaries fed distal to the infusion site, then some volume of the treatment bolus may be outside of the capillaries (and the target capillaries) when the occlusion stops bolus flow. Thus, the treatment bolus should generally be smaller in volume than the capillary bed to be treated.

Figure 2:
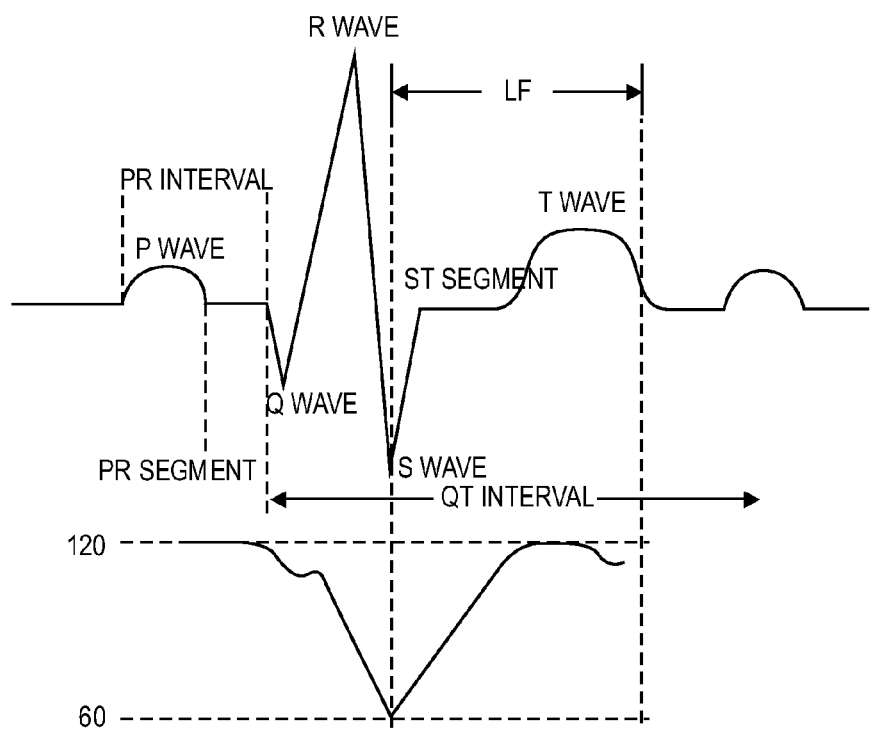
FIG. 2 illustrates an electrocardiogram waveform and a blood pressure waveform for a single cardiac cycle.

Referring to block 110 of FIG. 1, a low flow period of an artery may be determined based on electrocardiogram (ECG) cardiac cycle blood pressure and/or velocity sensor information. FIG. 2 shows an example ECG waveform or curve for a single cardiac cycle of a healthy patient. FIG. 2 also shows a blood pressure waveform or curve for the same patient.

Referring to the ECG curve in FIG. 2, the baseline or isoelectric line is represented as the straight line and reflects no positive or negative charges of electricity to create deflection. Under normal conditions, an electrical stimulus is generated by the sinus node located in the right atrium of the heart. The sinus node generates an electrical stimulus every time the heart beats (e.g., 60 to 190 times per minute, typically depending on the age and health of the patient). This electrical stimulus travels down through conduction pathways and causes the chambers of the heart to contract and pump out blood. The right and left atria are stimulated first and contract a short period of time before the right and left ventricle. The electrical impulse travels from the sinus node to the atria ventricular (AV) node, where it is delayed for a brief period, and continues down the conduction pathways via the bundle of HIS into the ventricles. The bundle of HIS divides into right and left pathways to provide electrical stimulation to both ventricles. As the electrical impulse moves through the conduction system, the heart contracts. Each contraction represents one heart beat. As noted, the atria contract a fraction of a second before the ventricles so that a bolus of blood is pumped into the ventricles, fully inflating them with blood before the ventricles contract.

Looking at the ECG in FIG. 2, the first upper notch of the ECG curve is called the "P wave." The P wave indicates that the atria are contracting to fully inflate the ventricles with blood. The next part of the curve is a short downward section connected to the tall upward section and small downward section. Collectively, this represents the "QRS complex." This part of the curve or tracing indicates that the ventricles have started contracting to pump out blood to the body. The next short upward segment of the curve is called the "ST segment." The ST segment indicates the amount of time from the beginning of the contraction of the ventricles to the beginning of the relaxation of the ventricles. The next upward curve is called the "T wave" and indicates the period of the relaxation ventricles.

In one embodiment, identifying a low flow period in a blood vessel according to the method presented with reference to FIG. 1 using an ECG curve such as shown in FIG. 2, involves identifying a period represented as "LF" between the S wave and the end of the T wave. It is during this period that the ventricle muscles relax and the flaps of the semilunar valve block blood flow into the coronary arteries. Thus, it is appreciated that either the ECG curve or a blood pressure curve or both may be used to identify low flow in a coronary blood vessel. Alternative methods to determine a low flow period include ultrasound or optical Doppler techniques. For example, a catheter may be inserted into a coronary blood vessel, the catheter having an ultrasound transducer. The transducer may be used to measure the velocity of blood flow by Doppler techniques. Alternatively, optical coherence tomography (OCT) associated with a catheter may also be used to measure velocity of blood flow by Doppler techniques (e.g., optical Doppler). Optical Doppler techniques are used to measure CFR. A still further method of measuring blood flow would be with an anenimeter. One anenimeter may be a heated wire inserted into a coronary blood vessel. It is appreciated that the wire will cool with blood flow. The rate of cooling may be used to determine blood flow.

Referring again to FIG. 1, having identified a low flow period of a blood vessel such as a coronary artery, one embodiment of a method includes introducing a treatment agent such as a cellular component during the low flow period of the blood vessel (block 120). By injecting the treatment agent into the blood vessel during the low flow portion of the cardiac cycle in the blood vessel, a greater concentration of treatment agent can be achieved at a treatment site, e.g., at an infarcted area of cardiac tissue (because less blood is flowing by during the injection to mix with the treatment agent). In addition, the treatment agent may be injected at a more rapid rate without increasing the pressure within the blood vessel as much as would the same injection rate during a high flow rate portion of a cardiac cycle.

In one embodiment, enough treatment agent is introduced (injected) to fill the desired blood vessel(s), including the arteries and arterioles associated with an infarcted area. As noted above, not all of the tissues fed by a recently occluded and now opened blood vessel (artery) will be ischemic, dead, or irreversibly damaged, because they may have been fed by different coronary arteries or artery branches. It is also known that as normal tissues become ischemic, their local arterioles become dilated, lowering the local flow resistance. In the embodiment described with respect to FIG. 1, the treatment agent is introduced at a point in time where normal tissues do not become ischemic. One way this is achieved is by introducing the treatment agent prior to or without occluding the blood vessel (artery) that may feed the normal (healthy) tissues as well as the infarcted tissues.

Referring again to FIG. 1, the treatment agent introduced in the blood vessel of block 120 may be introduced completely during a low flow period such as period LF in FIG. 2 (introduced within one heart cycle) or injected over a number of heart cycles. A typical blood flow in an artery varies from about two to five cubic centimeters per second. Therefore, to introduce three cubic centimeters of a treatment agent such as a cellular component, it is possible to introduce such amount in less than a second and thus, during the low flow period denoted as LF in FIG. 2. Alternatively, a treatment agent may be introduced for a longer period such as more than one heart beat (1.5 heart beats or more). In the latter case, any introduction (injection) at a higher flow period should be introduced at a lower flow rate than any introduction at a lower flow period to avoid an unacceptable increase in pressure in the blood vessel. In addition, the introduction (injection) could target low flow periods in consecutive cycles for the delivery of the majority of the treatment agent.

Following the introduction of a treatment agent, the method described in FIG. 1 includes occluding the blood vessel (block 130). A blood vessel may be occluded for a period to allow the treatment agent (e.g., cellular component) to be washed into the capillaries when the blood flow in the vessel is stopped. Because the occlusion occurs after the introduction of the treatment agent, most of the treatment agent should be resident in the capillaries during the occlusion prior to the start of ischemia of the normal tissues. It is also possible with the devices and techniques described below for almost instantaneously occluding a blood vessel that such occlusion may occur prior to or with the introduction of the treatment agent. One way this situation could occur is where an LF period is identified where a treatment agent can be introduced with a confidence that the treatment agent will be delivered to the desired capillaries prior to any ischemia of adjacent blood vessels can divert the treatment agent.

Figure 3:
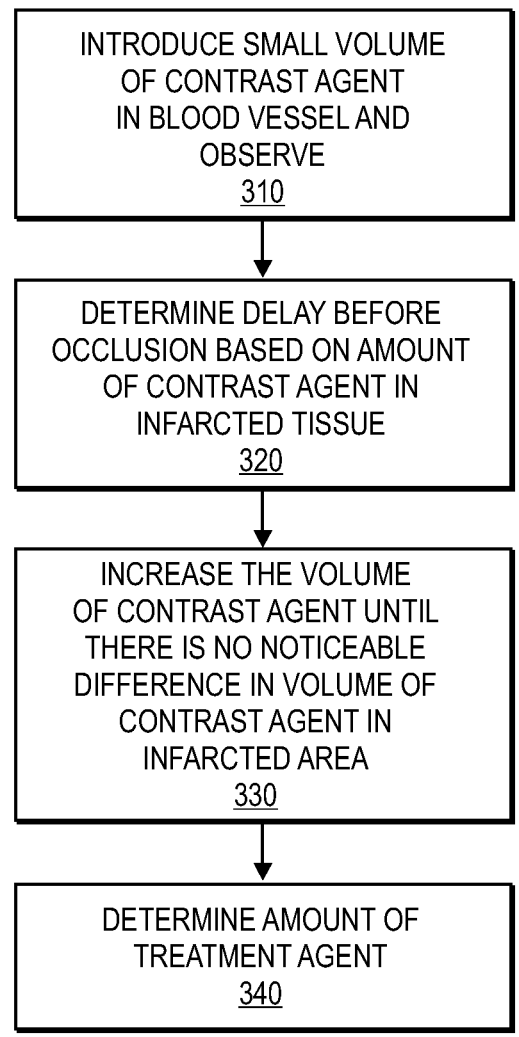
FIG. 3 shows a flow chart of a method of determining an amount of treatment agent and a delay time between the introduction of a treatment agent and occluding a blood vessel.

In the above embodiment, a method is described to introduce a treatment agent such as a cellular component into a blood vessel such that the treatment agent may flow into a desired region of capillaries associated with an infarcted area. One technique for determining the amount of treatment agent necessary according to the method described with respect to claim 1 is described in FIG. 3. FIG. 3 utilizes contrast agent to determine an amount of a treatment agent. A contrast agent is an agent that may be visualized externally, such as a radiopaque agent that may be observed through a fluoroscope.

Referring to FIG. 3, in one embodiment, the method includes introducing a contrast agent by way of, for example, a catheter into a blood vessel. The introduction (injection) may be set to be centered in a low period of the artery (such as period LF of FIG. 2) or, if the volume must be injected for a duration in excess of one cardiac cycle, such that the largest possible volume of the injection occurs during the low flow rate period(s). Initially, a small volume of contrast agent may be introduced (injected) into the blood vessel (block 310). Next, the method includes determining a delay before occlusion based on the amount of contrast agent in the infarcted tissue (block 320). By observing a radiopaque contrast agent with a fluoroscope, for example, the fluoroscope may be used to monitor the contrast agent and determine when the contrast agent is in the infarcted tissues. By injecting a small volume of contrast agent, and occluding at different (e.g., longer) periods after the introduction in repeated cycles, a delay time may be selected where the contrast agent in the infarcted tissues is greatest (e.g., a delay time that makes the infarcted tissues show the darkest, for the longest duration (during occlusion)). It is appreciated, depending upon how rapidly the occlusion device deploys, it is possible that the delay may be very small or negative (i.e., deployment of occlusion device must be initiated prior to the injection).

Following the determination of a delay before occlusion, the method of FIG. 3 includes increasing the volume of contrast agent until there is sufficient contrast agent in the infarcted tissues (block 330). One way this may be done is by increasing the volume of a radiopaque contrast agent until there is no noticeable difference in the darkness of the infarcted when viewed by a fluoroscope. Having determined the necessary volume of contrast agent, the volume may be tested using the delay determined at block 320. From this, the amount of treatment agent necessary may be determined (block 340).

The technique described above with reference to the method of FIG. 3 is one technique for determining an amount of a treatment agent, and a delay time prior to occlusion. Other techniques include techniques based on reference data, such as a size of the blood vessel at the point of introduction, the weight of the patient, and an externally measured blood flow parameter (ECG, blood pressure). In one embodiment, knowledge of at least two at the above factors will provide a good estimation of the amount of treatment agent and a delay time before occlusion.

FIGS. 4-9 illustrate one embodiment of a delivery device suitable for delivering a treatment agent including a cellular component such as described above. In this embodiment, delivery device 400 is a hollow guidewire having an occlusion device. Delivery device 400 includes hollow hypotube body 410 including proximal portion 405 and distal portion 415. Proximal portion 405 is intended to be resident outside of a patient during a procedure while distal portion may be percutaneously inserted, for example, into a femoral or radial artery and advanced to a treatment site via a transluminal root (e.g., an arteriole root) to a treatment site. A suitable treatment site is a coronary artery where, for example, a blockage in the coronary artery has previously been opened by way of an angioplasty procedure and it is desired to treat tissues distal to the blockage representatively referred to as an infarcted area. Hypotube body 410 of delivery device 400 includes a hollow lumen to allow a treatment agent to be introduced at a proximal port 420 through the lumen of hypotube 410 and exit at distal end 430 of hypotube 410. In one embodiment, hypotube 410 can be made of a metal-like 316L stainless steel, metal alloy, or polymer with an outer diameter and overall length of the hypotube comparable to most guidewires used for interventional procedures, including, but not limited to, an outer diameter of 0.012 inches, 0.014 inches, 0.018 inches and 0.035 inches. A suitable length includes, but is not limited to, 180 centimeters to 300 centimeters typical of guidewires for rapid exchange and over-the-wire applications, respectively, in interventional procedures.

In one embodiment, delivery device 400 includes cannula or tube 440 extending through the lumen of hypotube 410. Cannula 440 has a lumen therethrough and may be made of a flexible polymer material. In this embodiment, a proximal end of cannula 440 is defined by port 420 to introduce a treatment agent therethrough. A distal end of cannula 440 extends to end 430 of hypotube 410. In this manner, a treatment agent introduced through delivery port 420 is dispersed through a lumen of cannula 440 and exits delivery device at distal end 430. FIG. 5 shows a cross-section of delivery device 400 through lines 5-5' of FIG. 4. FIG. 5 shows hypotube 410 having a lumen therethrough and cannula 440, also having a lumen therethrough, disposed within the lumen of hypotube 410. In an embodiment where delivery device has an exit port at a distal end, the delivery device may also include one or more additional opening(s) radially disposed at a position proximal to the distal end of the device. These additional openings may act to diffuse an injection from the delivery device to minimize damage to the blood vessel.

In the embodiment shown in FIG. 4, treatment agent exits delivery device 400 at distal end 430. In another embodiment, delivery device 410 includes solid tip 450 of a flexible material such as might be used in guidewires in interventional procedures. In this embodiment, an exit point for a treatment agent such as a treatment agent introduced through cannula 440 may be at a position proximal to tip 450. FIG. 4 shows port 455 (shown in dashed lines) proximal to tip portion 450.

Delivery device 400 also includes occlusion device 460 positioned on hypotube 410. In this embodiment, occlusion device is an expandable cage-like structure that is shown in a collapsed configuration in FIG. 4. FIG. 4 also shows restraining sheath 470 disposed over hypotube 410 from proximal portion 405 to a distal portion beyond occlusion device 460. Restraining sheath 470 extends co-axially along hypotube 410.

In one embodiment, occlusion device as an expandable cage may be deployed by a physician by retracting restraining sheath 470 proximally to expose occlusion device 460. Once restraining sheath 470 is retracted, the self expanding cage of occlusion device 460 may immediately begin to expand. In a blood vessel, the occlusion device will expand until the device contacts a wall of the blood vessel. In one embodiment, delivery device 400 also includes obturator 475 affixed to a distal end of occlusion device 460. Obturator 475 may be implemented to inhibit possible "snow plowing" of occlusion device 460 or restraining sheath 470 as it is being delivered through the vasculature. For example, in one embodiment, in a collapsed configuration, occlusion device 460 has an outside diameter greater than an outside diameter of hypotube 410 to which occlusion device 460 is attached. This is illustrated in FIG. 6 which shows a cross-section of delivery device 400 through lines 6-6'. Obturator 475 is, for example, a soft polymeric material, such as PEBAX 40D, that has a smooth surface to assist the occlusion device travel through the vasculature while also inhibiting the distal end of restraining sheath 470 from digging or snow plowing into the wall of the blood vessel.

As noted above, occlusion device 460, in one embodiment, is an expandable cage-like structure. Suitable cage-like structures are described in the context of embolic filtering devices described in, for example, commonly assigned U.S. Publication No. 2003/0120303, filed Dec. 21, 2001; U.S. Publication No. 2003/0212361, filed Mar. 10, 2003; U.S. Publication No. 2004/0098032, filed Jun. 29, 2001; and U.S. Pat. No. 6,656,202, which are each incorporated by reference.

FIG. 7 shows an embodiment of occlusion device 460 in isolation. As illustrated in FIG. 7, occlusion device 460 is in a retracted state. Occlusion device 460 includes cage structure 480 of a number of struts and sheath 485 over cage structure 480. In this illustration, a portion of sheet 485 is cut away to reveal cage structure 480. Cage structure 480 is connected a distal end to obturator 475 and at a proximal end to collar 490. Details about occlusion device 460 are described below with reference to FIG. 9 and FIG. 10.

FIG. 8 shows delivery device 400 following the expansion of occlusion device 460. In one embodiment, delivery device is positioned within a blood vessel in the retracted state shown in FIG. 4 and FIG. 7. Representatively, delivery device 400 is advanced to a coronary artery such that occlusion device 460 is positioned proximal to a stenotic region where an angioplasty procedure had previously been performed to open the artery. Conventional imaging techniques may be used to place delivery device. In this manner, although not shown, delivery device 400 may include radiopaque markers that are visible under a fluoroscope or other markers (e.g., magnetic resonance imaging markers) to position delivery device 400 at a desired site within a blood vessel. Following the positioning of delivery device 400 within a blood vessel, occlusion device 460 may be deployed as desired. In this embodiment, occlusion device 460 is deployed by proximally retracting restraining sheath 470 to expose occlusion device 460 within the blood vessel. FIG. 8 shows delivery device 400 following the retraction of restraining sheath 470 approximately equivalent to the lengths of occlusion device 460. The retraction of restraining sheath 470 allows occlusion device 460 to deploy (expand). In one embodiment, occlusion device 460 expands immediately upon retraction of restraining sheath 470 without any external aid of force applied to occlusion device 460. Occlusion device 460 expands to an outer diameter of the blood vessel in which delivery device 400 is placed. The wall of a blood vessel may be used to constrain the expansion. Sheath 485 of occlusion device 460 may be selected of a material that inhibits permeation of blood flow past the occlusion device. Thus, occlusion device 460 when deployed may occlude a blood vessel and inhibit blood flow.

Figure 9:
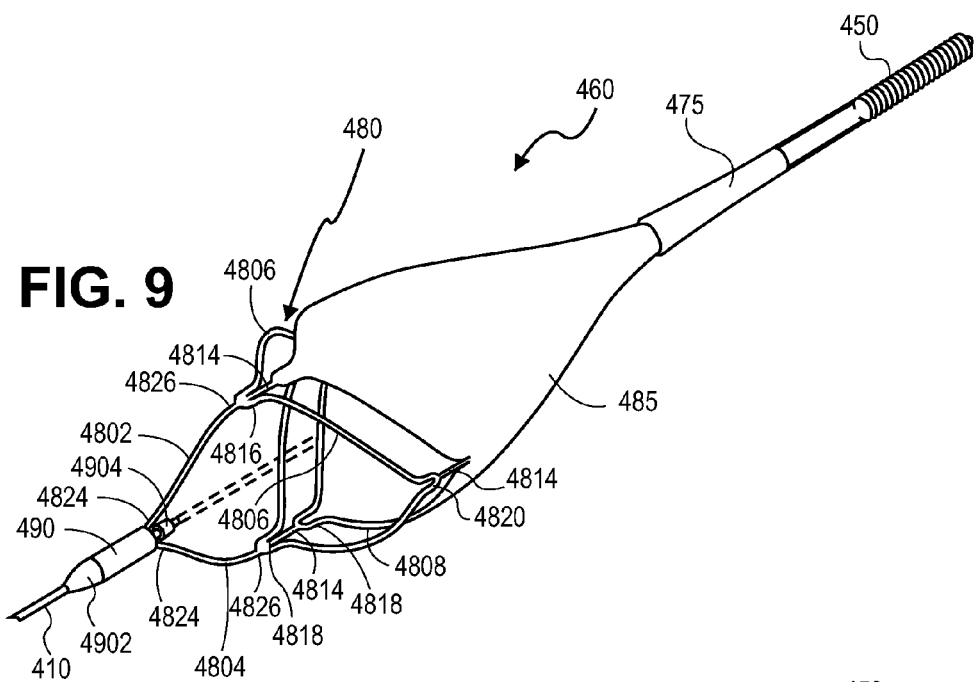
FIG. 9 shows a top side perspective view of the delivery device of FIG. 4 wherein the occlusion device is in an expanded configuration.
Figure 10:
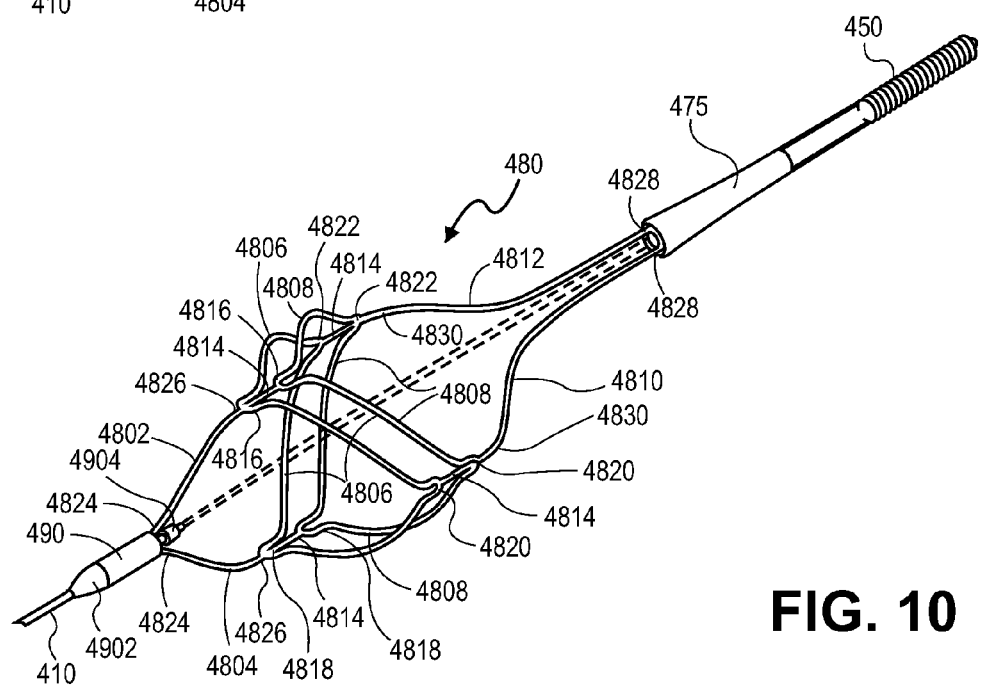
FIG. 10 shows a top side perspective view of the delivery device of FIG. 4 wherein the occlusion device is in an expanded configuration with a sheath over the occlusion device removed.

FIG. 9 and FIG. 10 show an example of occlusion device 460 of delivery device 400 in an expanded state, FIG. 9 shows occlusion device 460 with a portion of sheath 485 removed; FIG. 10 shows occlusion device 460 with sheath 485 completely removed. The following description of an embodiment of cage structure 480 is similar to the description of a cage structure for an embolic filtering device described in U.S. Publication No. 2003/0120303 which is incorporated by reference. It is appreciated that the cage structure presented herein is representative of similar structures described in the referenced application as well as the other applications and patent referenced above which are also incorporated by reference.

Referring to FIG. 9 and FIG. 10, expandable cage structure 480 of occlusion device 460 includes a pair of self-expanding proximal struts 4802 and 4804 that help to deploy occlusion device 460 and the remainder of the expandable cage. Proximal struts 4802 and 4804 are connected to first circumferential member 4806 which is adapted to move from an unexpanded delivery position (FIG. 4 and FIG. 7) to the expanded deployed position (FIG. 8). Second circumferential member 4808 is, in turn, connected to first circumferential member 4806. The deployment of first circumferential member 4806 and second circumferential member 4808 results in occlusion device 460 being placed against a wall of an artery or other blood vessel, even if the lumen of the blood vessel is non-circular. A pair of distal struts 4810 and 4812 connected to second circumferential member 4808 extend distally toward obturator 475. First circumferential member 4806 and second circumferential member 4808 are connected to, and spaced apart, from each other by short connecting struts 4814. It should be appreciated that a single circumferential member could be used to create an expandable cage. Also, additional circumferential members could be added to create a larger expandable cage. Additionally, while two proximal struts and distal struts are shown in the cage design of FIGS. 9-10, the cage could also be made with a single proximal and distal struts or additional struts could be implemented. As can be seen in FIGS. 9-10, each circumferential member includes four bending regions, 4816, 4818, 4820 and 4822 formed on the circumferential member to enhance the performance of the circumferential member to bend as it moves between an unexpanded and an expanded position. In the embodiment shown in FIG. 10, each bending region 4816, 4818, 4820 and 4822 is placed on the circumferential member approximately 90 degrees apart. Each of the proximal struts includes a first end 4824 attached to collar 490 which is rotatably mounted to hypotube 410. Each proximal strut includes second end 4826 connected to one of the proximal bending regions 4816 and 4818 of first circumferential member 4806. These proximal bending regions 4816 and 4818 are spaced approximately 180 degrees apart from each other along a circular diameter defined by circumferential member 46 in an expanded state. Each of distal struts 4820 and 4822, in turn, have first end 4828 connected to and extending towards obturator 475 and a second end 4830 attached to distal bending regions 4820 and 4822 of second circumferential member 4808. These distal bending regions 4820 and 4822, in turn, are spaced approximately 180 degrees apart from each other and are offset 90 degrees from proximal bending regions 4816 and 4818.

Each of the bending regions is substantially U-shaped which help to create a natural bending point on the circumferential member. While the flexibility of the circumferential member is already high, these bending regions only help to increase the ability of the circumferential member to collapse or expand when needed. In this manner, the shape of the hinge region creates a natural hinge that helps to actuate the expandable cage between an unexpanded and an expanded position. As shown in FIG. 10, U-shaped bending regions 4814 and 4816 are positioned directly opposite the U-shaped portion of distal bending regions 4818 and 4820. The positioning of the direction of the U portion also enhances the ability of the circumferential member to bend. Circumferential member 4816 and circumferential member 4818, while being bendable, nevertheless may maintain sufficient radial strength to remain in the deployed position to hold occlusion device 460 open in a blood vessel for occluding blood flow.

The shape of the bending regions are shown as substantially U-shaped portions, however, any one of a number of different shapes could be utilized to create a natural bending point on a circumferential member. For example, a V-shaped region could also be formed and would function similarly to a U-shaped portion to facilitate the collapse and expansion of a circumferential member as needed. Alternative shapes and sizes of the bending regions could also be utilized. Although four bending regions are shown on each circumferential member, it is appreciated that the number of bending regions could be increased or decreased as needed. For example, it is possible to utilize only two bending regions. Additional bending regions also could be utilized in the event that additional proximal or distal struts are used to form the expandable cage. Moreover, different sizes, shapes and location of the bending regions can be utilized on any circumferential member.

In the embodiment shown in FIGS. 9-10, expandable cage structure 480 is shown rotatably mounted to a distal end of hypotube 410 to allow the entire occlusion device 460 to remain stationary once deployed in a blood vessel. This feature prevents the occlusion device from rotating in the event that the proximal end of hypotube 410 is rotated by the physician during use. As a result, the possibility that the deployed occlusion device can be rotated to cause trauma to a wall of a blood vessel minimized. Referring to FIG. 9 and FIG. 10, first end 4824 of proximal struts 4802 and 4804 are attached to collar 490 which is rotatably mounted on hypotube 410 between a pair of stop fittings 4902 and 4904. Stop fittings 4902 and 4904 allow expandable cage structure 480 to spin on hypotube 410 but restrict the longitudinal movement of the cage on the hypotube. A distal end of cage structure 480 may be connected to obturator 475 which may similarly be free to rotate on hypotube 410.

An expandable cage such as shown in detail with reference to FIG. 9 and FIG. 10 may be made in a variety of ways. One particular method of making the case is to cut a thin-walled tubular member, such as nickel-titanium hypotube, to remove portions of the tubing in a desired pattern for each strut, leaving relatively untouched the portions of the tubing which are to form each strut. The tubing may be cut into the desired pattern by means of a machine-controlled laser. The tubing used to make the cage could possibly be made of suitable biocompatible materials such as spring steel. Elgiloy is another material which could possible be used to manufacture the cage. Also, certain polymers could be used.

In one embodiment, a strut size is relatively small, so the tubing from which the cage is formed may have a small outside diameter. Typically, the tubing has an outside diameter on the order of about 0.02 to about 0.04 inches in an unexpanded condition. Also, the cage can be cut from large diameter tubing. Fittings are attached to both ends of the lased tube to form the final cage geometry. One suitable wall thickness of tubing is about 0.076 millimeters (about 0.001 to about 0.006 inches). As can be appreciated, the strut widths and/or depths at the bending point may be less. Further details of manufacturing a cage such as shown in FIG. 9 and FIG. 10 may be found with reference to the above-noted applications and patent describing embolic filtering devices. In the embodiment described, expandable cage structure 480 is covered by sheath 485. Sheath 485 may be a polymeric material such as, but not limited to, polyurethane or GORTEX®, a commercially available material. Other suitable materials include expanded polytetrafluoroethylene (ePTFE). The material may be elastic or non-elastic. A suitable wall thickness of sheet 485 can be about 0.005 inches. The wall thickness may vary depending on the particular material selected. The material can be made into a cone or similarly size shape utilizing blow-mold technology or dip technology. Additionally, a material for sheath 485 can have a "set" put in a much like the set used in dilation balloon to make the sheet rewrap more easily when placed in the collapsed position shown in FIG. 1.

Referring again to FIG. 4 and FIG. 7, suitable materials for restraining sheath 470 can be polymer material such as cross-linked high density polyethylene (HDPE). Restraining sheath 470 can alternatively be made from a material such as a polyolefin that has sufficient strength to hold the compressed occlusion device 460 and has relatively low frictional characteristics to minimize any friction between the occlusion device and the sheath. Friction can be further reduced by applying a coat of silicone lubricant, such as MICROGLIDE®, to the inside surface of the restraining sheath before the sheath is placed over occlusion device 460.

Figure 11:
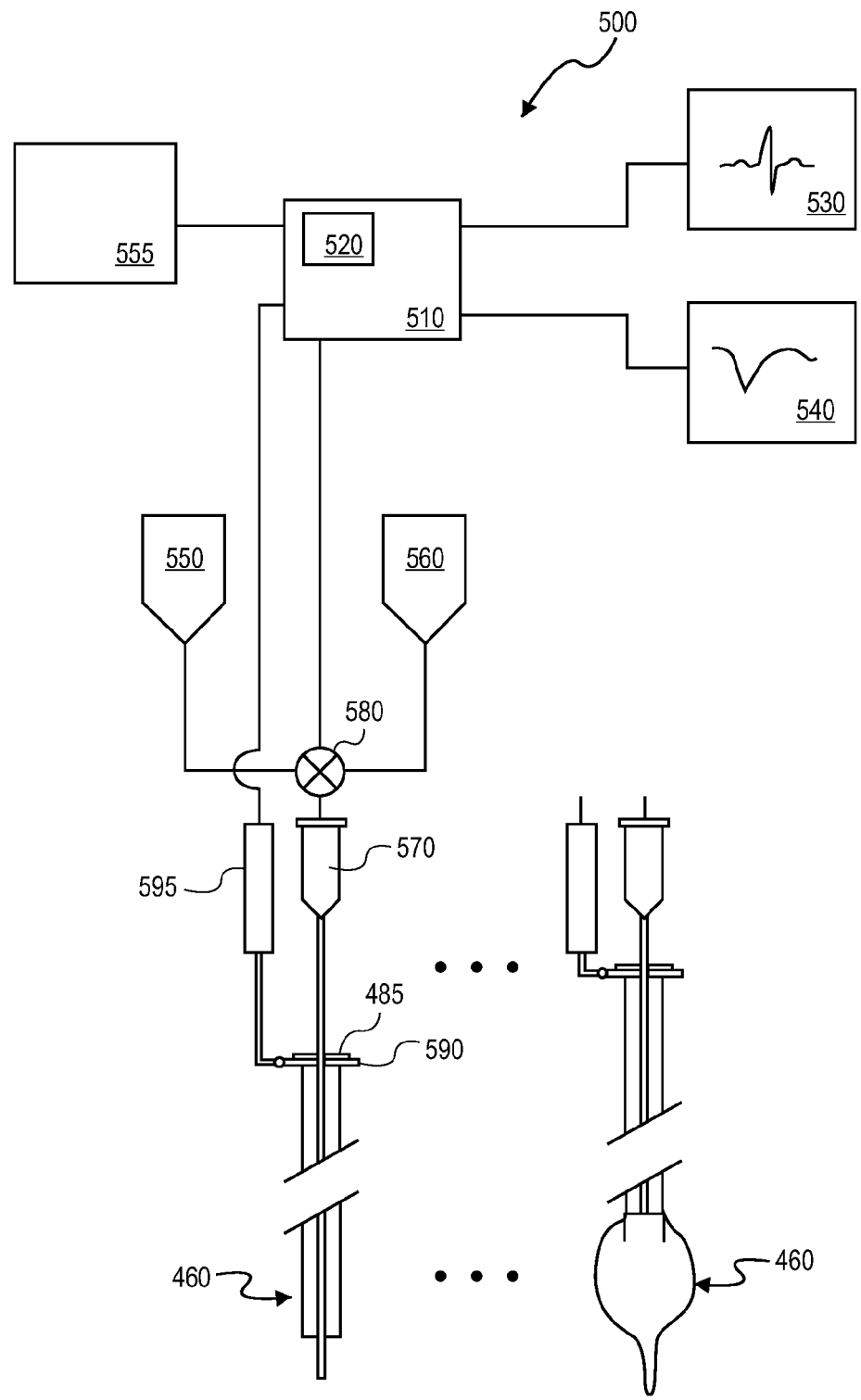
FIG. 11 shows the schematic front view of a system for delivering an agent to a blood vessel utilizing the delivery device shown with reference to FIGS. 4-10.

FIG. 11 schematically illustrates a system for controlling the introduction of contrast agent/treatment agent through a delivery device and the expansion/retraction of an occlusion device according to one embodiment. In one embodiment, system 500 includes controller 510 that contains a suitable algorithm to introduce contrast agent/treatment agent and to expand and retract an occlusion device, such as occlusion device 460.

Controller 510 is supplied with software instruction logic that is a computer program stored in a machine-readable medium such as memory 520 in controller 510. The memory is, for example, a portion of a hard disk drive. Controller 510 may also be connected to a user interface that allows an operator to enter certain parameters, such as a desired volume of treatment agent, a delay time for occlusion, etc. In one embodiment, however, system 500 itself may calculate the amount (volume) of a treatment agent, as well as a delay time prior to occlusion following the method described above with reference to FIG. 3. Thus, the instruction logic may include logic to perform the method described with respect to FIG. 3. Accordingly, controller 510 may be connected to and receive data from cardiac cycle sensor monitors such as ECG 530 and/or blood pressure monitor 540. Although shown in waveform, it is appreciated that such data may be readily converted, if necessary, to a digital format. One way is to convert data regarding portions of a curve into a text format by expressing the waveform data in terms of numerical value determined at a certain time interval. Any other implementation at least a portion of the waveform may be expressed in terms of a function (e.g., a derivative) of waveform data at various time periods.

Referring to the method described with reference to the method of FIG. 3, system 500 (FIG. 11) can identify a low flow time in, for example, an artery for an injection of contrast agent or a treatment agent during a single cardiac cycle. On the other hand, using the data obtained from cardiac cycle sensor information, controller 510 may adjust system 500 so that the largest possible part of an injection occurs during low flow rate.

System 500 may then set a representative injection duration of a volume of contrast agent to be delivered from reservoir 550. Controller 510 actuates control valve 580 and using, for example, a volumetric flow meter, can establish a suitable amount of contrast agent from reservoir 550 to be injected according to block 310 of the method described with reference to FIG. 3.

Using the method described in FIG. 3 to describe system 500 in FIG. 11, having introduced the contrast agent, system 500 may then determine a delay before occlusion of the blood vessel based on the monitoring of contrast agent in infarcted tissue according to block 320 of the method of FIG. 3. Referring to system 500, in one embodiment, the contrast agent in reservoir 550 is a radiopaque material. Fluoroscope 555 may be connected to controller 510. Controller 510 may receive data from fluoroscope 555 indicating an amount of contrast agent in infarcted tissue. This may be done, for example, by assigning an area to infarcted tissue and numerical values for amounts of contrast agent within the assigned area. System 500 also includes clamp 590 and actuatable control arm 595 connected to the but clamp 590 and to controller 510. Clamp 590 may be connected to a proximal end of restraining sheath 485 (see FIG. 4). In one embodiment, clamp 590 is a C clamp that engages a lip on a proximal end of restraining sheath 485. When actuated by controller 510, control arm 595 pulls clamp 590 and thus restraining sheath 485 toward its housing (as viewed). The actuation of control arm 595 can be almost instantaneous using an electrical mechanism which corresponds to a nearly instantaneous opening of occlusion device source 60 within the blood vessel. Controller 510 may store instructions to retract control arm 595 for a period of time determined to be a sufficient dwell time or indicative of a suitable dwell time for a treatment agent to reside in capillaries of infarcted area.

Referring again to the method of FIG. 3 in the context of the description of the FIG. 11, using system 500, an amount or a volume of contrast agent may be introduced until there is no noticeable difference in volume of the contrast agent in the infarcted area (block 330). This data may be received in controller 510 and possibly stored in memory 520. Based on that determined volume, system 500 may repeat an injection of contrast agent in the volume determined in block 330 according to the delay determined in block 320. This data may also be stored in memory 520 or otherwise in controller 510. Once an appropriate volume for a treatment agent is determined using simulated injections of contrast agent and a suitable delay time for opening occlusion device 460 is determined, system 500 may be configured to switch from contrast agent (from reservoir 550) to a treatment agent from reservoir 560.

In the above embodiment described above with reference to FIGS. 4-10, a delivery device was described of a hollow guidewire. It is appreciated that other devices, including catheter devices may similarly be suitable. FIGS. 12-15 shows an example of a single cannula catheter device. Referring to FIG. 12, FIG. 12 shows delivery device 600 including cannula 610 of a polymeric material in the form of cylindrical tube a representative length of cannula 610 is on the order of 180 centimeters to 300 centimeters. Cannula 610 defines proximal portion 605 and distal portion 615 of delivery device 600. In one embodiment, proximal portion 605 is intended to be resident outside of a patient during a procedure. Distal portion 615 is intended to be inserted to, for example, a femoral or radial artery into a patient and advanced to a treatment site, such as a coronary artery where a prior angioplasty procedure has taken place. In one embodiment, cannula 610 has a lumen therethrough having a diameter sufficient to be advanced to a treatment site over a guidewire. Representatively, cannula 610 has a lumen having an interior diameter of at least about 0.012 inches to about 0.036 inches or more. In one embodiment, a contrast agent or a treatment agent is intended to be introduced in delivery port 620 at a proximal end of cannula 610. Delivery port 620 is, for example, a female luer lock fitting. Cannula 610 includes distal end 630 that may have an opening. In this embodiment, a distal portion of cannula 610 not only includes opening 630 at a distal end of cannula 610 but also one or more openings 635 spaced radially near the distal end of cannula 610. This additional opening(s) may be used as an exit port(s) for a contrast agent or a treatment agent and may serve, in one embodiment, to diffuse an injection through cannula 610 to avoid damaging a blood vessel.

Similar to a catheter described above with reference to FIGS. 4-10, delivery device 600 includes occlusion device 660 co-axially disposed on cannula 610. FIG. 12 shows occlusion device 660 in a retracted or restrained configuration. In one embodiment, occlusion device 660 is restrained by restraining sheath 670 placed over the occlusion device. In one embodiment, occlusion device 660 includes a cage structure such as cage structure 480 described with reference to FIGS. 9-10 and sheath 485 overlying the cage structure. In this manner, occlusion device 660 may be opened almost instantaneously with the proximal retraction of restraining sheath 670.

FIG. 13 shows a cross-section of delivery device 600 through lines 13-13' and shows the hollow tubular structure of cannula 610. FIG. 14 shows a cross-section through lines 14-14' of delivery device 600 and illustrates occlusion device 660 on cannula 610 and restraining sheath 670 over occlusion device 660.

In one embodiment, occlusion device 660 of a cage structure may be connected to an exterior of cannula 610 by, for example, affixing (e.g., glue or thermal bond) obturator 675 to cannula 610 and attaching the cage structure to obturator 675. A proximal end of occlusion device 660 may be connected to cannula 610 through collar 690.

FIG. 15 shows occlusion device 600 following the proximal retraction of restraining sheath 670. In this embodiment, restraining sheath 670 is proximally retracted a length sufficient to expose occlusion device 660. Following exposure, for example, in a blood vessel occlusion device 660 expands (through an expansion of the cage structure) to a diameter equivalent to an interior diameter of a blood vessel in which it is resident.

The above described delivery device is another example of a suitable delivery device for delivering a treatment agent such as, but not limited to, a cellular component where the delivery device includes an occlusion device that may be opened almost instantaneously, e.g., wherein a time for occlusion of a blood vessel is dependent on the time it takes for a cage structure to change from a collapsed position to an expanded position on liberation. An advantage of such immediate or almost instantaneous expansion of an occlusion device in the delivery devices described is it eliminates the delay time associated with, for example, dilating a balloon as known in the art. It is, however, appreciated that the method described with respect to FIG. 1 and FIG. 3 as well as the system described with respect to FIG. 11 may be utilized in connection with a traditional occlusion devices, such as a balloon.

The above described embodiments may be used in conjunction with the treatment of discreet stenoses in blood vessels such as coronary artery. The techniques, while not directly treating discreet stenoses, address the issue of diffuse injury or disease and/or less occlusive vulnerable plaques that may occur in conjunction with a target lesion that presumably caused the ischemic symptoms associated with the discreet stenoses. The following embodiments describe devices and techniques for simultaneously or sequentially treating a target lesion in a blood vessel as well as an infarcted area and/or distressed area and/or a less occlusive vulnerable plaque.

FIG. 16 shows a schematic side view of a delivery device suitable for delivering a stent to address a target lesion as well as a treatment agent, including a cellular component, to a position in the blood vessel distal to the target lesion. FIG. 16 shows delivery device 700 having a distal portion disposed within blood vessel 705. Blood vessel 705 is, for example, a coronary artery. In this embodiment, blood vessel 705 includes target lesion 707 that may have been previously treated through a percutaneous transluminal angioplasty (PCTA) procedure. Delivery device 700 is, in one embodiment, a drug eluting stent catheter system suitable to deploy a stent. Delivery device 700 includes primary cannula or tube 710 extending from proximal portion 712 to distal portion 713. In one embodiment, proximal portion 712 is intended to be resident outside of a patient's body during a treatment while distal portion may be advanced, for example, through a femoral or radial artery to a treatment site within a coronary artery (e.g., blood vessel 705).

Referring to FIG. 16, delivery device 700 includes guidewire cannula 735 extending from a proximal end of proximal portion 712 to a distal end of distal portion 713. Guidewire cannula 735 is representatively, a polymer material having a lumen therethrough to allow delivery device 700 to be advanced to a treatment site in an over-the-wire (OTW) fashion over a guidewire (not shown). A guidewire may be retracted and removed through port 7350 at a distal end of delivery device 700 once the delivery device is positioned where desired.

In the embodiment shown in FIG. 16, delivery device 700 includes balloon 720 incorporated at distal portion 713 of delivery device 700 and connected to a distal end of primary cannula 710. Balloon 720 is an expandable body in fluid communication with inflation cannula 730 disposed within primary cannula 710. One suitable material for balloon 720 is an elastomeric nylon such as PEBAX™, a condensation polymerized polyether block polyamide. PEBAX™ is a trademark of Atochem Corporation of Puteaux, France. Other suitable materials for balloon 720 include, but are not limited to, a biocompatible blend of polyurethane and silicone or a styrenic block copolymer (SBC) or blend of SBCs. Inflation cannula 730 extends from balloon 720 within distal portion 713 to inflation port 7330 at a proximal end of proximal portion 712. Inflation cannula 730 may be used to deliver a fluid through its lumen to inflate balloon 720. In a delivery configuration, balloon 720 is in a non-expanded or deflated state. FIG. 16 shows balloon 720 in an expanded or inflated configuration (i.e., after the introduction of a fluid through inflation cannula 730).

One way to form a distal portion of delivery device 700 is to connect a distal end of balloon 720 to guidewire cannula 735 through, for example, a thermal seal (e.g., heat fusion). Guidewire cannula 735 and inflation cannula 730 may extend from a distal end of primary cannula 710. A proximal end of balloon 720 may be connected to a distal end of primary cannula 710 so that a portion of inflation cannula 730 and guidewire cannula 735 are within balloon 720. In one embodiment, balloon 720 may have one or more radio-opaque markers applied to its outer diameter, such as by adhesive, laser bonding, or heat bonding, and/or may include a filler such as barium sulfate added to the polymer to form balloon 720 to track the position of balloon 720 in a blood vessel under a fluoroscope. It is appreciated that alternative markers/identifiers and imaging techniques may be used.

Overlying balloon 720 in the embodiment shown in FIG. 16 is stent 725. In one embodiment, stent 725 may be a metal or polymeric stent that has dimensions suitable to encompass target lesion 707 within blood vessel 705. In other words, stent 725 has a length dimension that is sufficiently greater than a length dimension of lesion 707 so that when a stent is deployed, ends of the stent may contact healthy tissue. In one embodiment, stent 725 is a drug eluting stent.

Delivery device 700 may be inserted into a blood vessel such as blood vessel 705 with stent 725 on balloon 720 and each of balloon 720 and stent 725 in a non-expanded configuration. Visualization techniques such as may be used to place delivery device in such a way balloon 720 and stent 725 are positioned at a desired treatment site approximately adjacent (longitudinally encompassing) lesion 707.

FIG. 16 shows delivery device 700 following the inflation of balloon 720 to deploy stent 725 at a treatment site including lesion 707. In addition to its use deploying stent 725, delivery device 700 may also be utilized to deliver a treatment agent to the blood vessel or an infarcted area distal to lesion 707 via capillaries and arterioles distal to the lesion. Thus, in one embodiment, in conjunction with or immediately after a deployment of stent 725, a treatment agent(s), may be introduced through a lumen of guidewire cannula 735. In this manner, a solution (e.g., a suspension) including a treatment agent may be connected to proximal port 7350 of guidewire cannula 735, following the removal of a guidewire for introduction into blood vessel 705. A treatment agent may be, for example, a small molecule drug, protein, peptide, or gene construct in solution or in suspension within a controlled-release microsphere or liposome formulation. Suitable treatment agents include, but are not limited to, everolimus, statins, oxidant signal antagonists, eNOS regulators, or TIMMPS. In one embodiment, the infusion will be a solution or controlled-release suspension of a treatment agent in microspheres and/or nanospheres or liposomes to address the regional disease or injury.

FIG. 17 shows another embodiment of a delivery device. In this embodiment, delivery device 800 is similar in many respects to delivery device 700 and may be used to deploy a stent. Representatively, delivery device 800 includes primary cannula 810 extending from proximal portion 812 to distal portion 813, the distal portion intended to be resident in a patient during a treatment with the proximal portion resident outside the patient. Disposed within a lumen of primary cannula 810 is guidewire cannula 835 extending from a proximal end (at proximal port 8350) to a distal end of delivery device 800 in an over-the-wire (OTW) configuration. Primary cannula 810 also includes inflation cannula 830 extending from a proximal end (at port 8330) to a position within balloon 820. Balloon 820 is connected to a distal end of primary cannula 810. In one embodiment, a fluid may be introduced through a lumen of inflation cannula 830 to inflate balloon 820 to position stent 825 within blood vessel 805. As illustrated, stent 825 is positioned adjacent lesion 807 within lumen 805. Balloon 820 of delivery device 800 is shown in a non-expanded or deflated state following the deployment of stent 825.

In the embodiment shown in FIG. 17, delivery device 800 includes occlusion device 860 positioned on guidewire cannula 835. Thus, guidewire cannula 835 extends a distance (e.g., three to six centimeters) from a distal end of balloon 820 sufficient to accommodate occlusion device 860 on guidewire cannula 835 distal to balloon 820. In the embodiment illustrated, occlusion device 860 is an expandable cage structure covered by a sheath, similar to the cage structure described with reference to FIGS. 4-15 and the accompanying text. Delivery device 800 also includes restraining sheath 870 over guidewire cannula 835. Balloon 820 is connected (e.g., thermally sealed) at a distal end to restraining sheath 870. Restraining sheath 870 extends from proximal portion 812 of delivery device 800 to distal portion 813 in such a manner that restraining sheath 870 has a length, in one embodiment, to encompass occlusion device 860. In the embodiment shown in FIG. 17, restraining sheath 870 is retracted (moved proximally a distance, D) to expose occlusion device 860. Since a retraction of restraining sheath 870 will also result in the movement of balloon 820 (where balloon 820 is connected to restraining sheath 870), balloon 820 is deflated prior to retraction. Upon retraction of restraining sheath 870, occlusion device 860 may move from a collapsed configuration to an expanded configuration as shown.

Referring to the embodiment shown in FIG. 17, representatively, delivery device 800 may be used to deploy stent 825 via balloon 820. Subsequent to a deployment of stent 825, balloon 820 is deflated and occlusion device 860 may be expanded to occlude blood vessel 805 and a treatment agent, such as a drug, protein, peptide, gene construct, or cellular component, possibly in or combined with micro- and/or nanoparticles, may be introduced through guidewire cannula 835 (e.g., once a guidewire has been removed).

In one embodiment, occlusion device 860 may be deployed and a treatment agent delivered through a lumen of guidewire cannula 835 at a low flow period in the blood vessel so that the treatment agent may flow distally (distal from lesion 807) to capillaries and/or arterioles associated with the blood vessel in a similar manner as described above with reference to FIGS. 4-8 and the description therein. Thus, in one embodiment, the method described with respect to FIGS. 1 and 3 may be followed.

In the embodiment described with respect to FIG. 16 and FIG. 17, the introduction of the treatment agent is described with respect to treating diffuse disease or injury and/or less occlusive vulnerable plaques in conjunction with a stenting procedure of an upstream lesion. In each of the embodiments, the same delivery device or catheter is used to deploy a stent and introduce a treatment agent in the blood vessel downstream from the target lesion.

Figure 18:
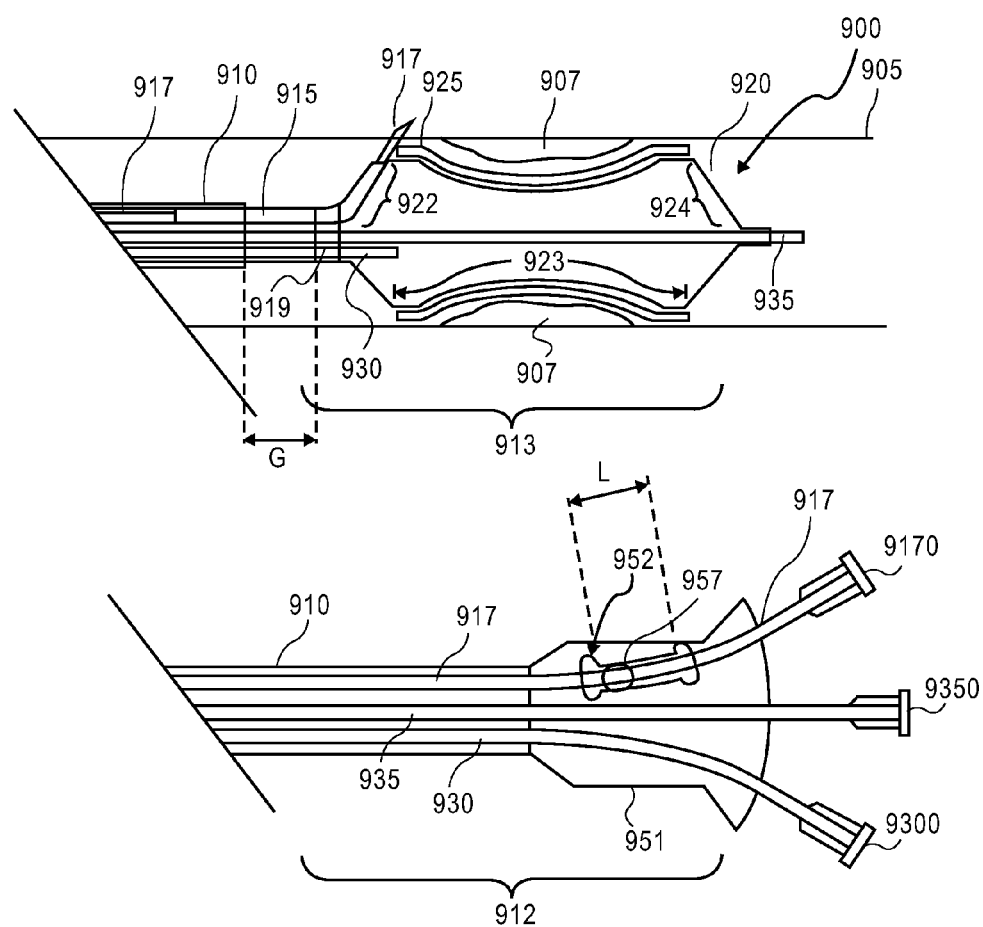
FIG. 18 shows a cross-sectional side view of another embodiment of a delivery device in a blood vessel deploying a stent and capable of releasing of a treatment agent.

FIG. 18 shows another embodiment of a delivery device suitable for deploying a stent to treat a target lesion as well as introducing a treatment agent to address diffuse disease and/or less occlusive vulnerable plaques. Delivery device 900 is a catheter device including proximal portion 912 intended to be resident outside of a patient during a procedure and distal portion 913 intended to be resident within a blood vessel of a patient during a procedure. FIG. 18 shows delivery device 900 having distal portion 913 positioned within blood vessel 905. Delivery device 900 includes primary cannula 910 extending from proximal portion 912 to distal portion 913. Primary cannula 910 has a lumen therethrough. Disposed within a lumen of primary cannula 910 is guidewire cannula 935. Guidewire cannula 935 extends from a proximal end of delivery device 900 (at port 9350) to a distal end of the delivery device in an over-the-wire (OTW) configuration. Alternatively, guidewire cannula 935 may extend only through a distal portion of delivery device 800. Guidewire cannula 935 has a lumen therethrough suitable to allow delivery device to be maneuvered over a guidewire to a region of interest within a blood vessel. A guidewire is not shown.

Delivery device 900 also includes balloon 920 connected at a distal end of primary cannula 910. Delivery device 900 also includes inflation cannula 930 extending from a proximal end (at port 9330) to a portion within balloon 920. In one embodiment, balloon 920 may be expanded by introducing a fluid through a lumen of inflation cannula 930. In the embodiment shown in FIG. 18, balloon 920 may be expanded to position stent 925 over or adjacent lesion 907. Thus, balloon 920 is also used to deploy stent 925 to a target site.

In addition to deploying stent 925 adjacent a target lesion, delivery device 900 includes at least one needle cannula to allow a needle to be injected into a wall of the blood vessel. Referring to FIG. 18, balloon 920 includes proximal taper wall 922, medial working length 923 and distal taper wall 924. Balloon 920 may be made of a variety of polymer materials. Suitable materials for balloon 920 include, but are not limited to, an elastomeric nylon such as PEBAX™, a biocompatible blend of polyurethane and silicone or a SBC or blend of SBCs. Proximal taper wall 922, medial working length and distal taper wall 924 can be bound together by seams or be made out of a single seamless material.

Delivery device 900, in the embodiment shown in FIG. 18, also includes at least one needle cannula. Needle cannula 915 is connected to proximal taper wall 922 of balloon 920 and extends at a proximal end, in one embodiment, into a portion of primary cannula 910. Representatively, a suitable length for needle cannula 915 is on the order of three to 6.5 centimeters (cm). Delivery device 900 also includes needle 917. Needle 917 extends from distal portion 913 to proximal portion 912 of delivery device 900. At distal portion 913, needle 917 is disposed through a lumen of needle cannula 915. Thus, a dimension of needle cannula 915 is selected to allow a needle to be moved therethrough. Representatively, needle cannula 915 has an inner diameter (lumen diameter) on the order of 0.04 cm and an outer diameter on the order of 0.6 cm. In the illustrated embodiment, a single needle cannula is needle shown with delivery device 900. In other embodiments, a delivery device may include more needles (e.g., two or more). In multiple (two or more) needle assemblies, the needle may be oriented with respect to one another according, representatively, to the purpose sought to be achieved by the delivery assembly. Representatively, needles may be placed adjacent to one another or circumferentially spaced around a proximal taper wall of a balloon.

FIG. 18 shows needle cannula 915 connected to an exterior surface of balloon 920. Specifically, a distal end of needle cannula 915 extends to a point equivalent to or less than a length of proximal taper wall 922 of balloon 920. One suitable technique for connecting needle cannula 915 of a polymer to balloon 920 is through an adhesive. A suitable adhesive includes a cyanocrylate (e.g., LOCTITE 414™) adhesive, particularly where the balloon material is a PEBAX™ material.

Delivery device 900 in the embodiment shown in FIG. 18 also includes sheath ring 919. Sheath ring 919 is positioned over, in this embodiment, guidewire cannula 935, inflation cannula 930, and needle cannula 915. In one embodiment, sheath ring 919 functions to inhibit delamination of needle cannula 915 from proximal taper wall 922 of balloon 920. Thus, a distal end of sheath ring 919 is placed, in one embodiment, at a point immediately proximal to where needle cannula 915 will rotate, bend or plicate in response to the expansion of balloon 920. In one embodiment, sheath ring 919 is a biocompatible material that is capable connecting to (e.g., bonding to) a material for balloon 920 and to a material for each of the noted cannulas that it surrounds. One suitable material is a polymer material similar to one or more of the cannulas and/or balloon 920. An example of a suitable material is PEBAX 40D™ tubing material having an inner diameter 0.012 cm and an outer diameter of 0.13 cm. Representatively, a body of sheath ring 919 has a length from a proximal end to a distal end on the order of 0.25 millimeters (mm) to 0.75 mm. A distal end of sheath ring 919 is positioned proximally adjacent to a determined plication or bend or rotation point of delivery cannula 915. In one aspect, a gap, G, between sheath ring 919 and primary cannula 910 provides flexibility at a distal end of delivery device 900. In another embodiment, there may be no gap (G=0) between sheath ring 919 and primary cannula 910.

One way to form delivery device 900 including sheath ring 919 is to initially connect (e.g., bond) balloon 820 at a distal end to guidewire cannula 935. Balloon 920 is also connected (e.g., bonded) at a proximal end to guidewire cannula 935 and inflation cannula 930. One way to connect balloon 920 at a distal end to guidewire cannula 935 and at a proximal end to guidewire cannula 935 and inflation cannula 930 is through a thermal seal (e.g., heat fusion).

Once balloon 920 is sealed at each end, balloon 920 is inflated. Proximal taper wall 922 can taper at any suitable angle, typically between 15° to less than about 90°, when balloon 920 is in an expanded (inflated) configuration. Delivery cannula 915 is aligned on inflated balloon 920 with a distal end corresponding to a distal end of proximal taper wall 922 of balloon 920. A distal end of needle cannula 915 may be tapered to a proximate or match a plane defined by medial working length 923 of balloon 920 when balloon 920 is in an expanded (inflated) state. Delivery cannula 915 may then be glued or affixed to balloon 920 through an adhesive such as a cyanocrylate adhesive. Next, sheath ring 919 is loaded (advanced proximal to distal) onto a proximal end of balloon 920 and the cannulas of delivery device 900 (e.g., guidewire cannula 935, inflation cannula 930, needle cannula 915). A material of sheath ring 919 of a polymer such as PEBAX 40D™ may be connected to balloon 920 and needle cannula 915 by a thermal seal process.

Referring to FIG. 18, proximal portion 912 of delivery device 900 is intended, in one embodiment, to reside outside a patient while the remainder of the delivery device is percutaneously introduced into, for example, the cardiovascular system of a patient via a brachial, radial or femoral artery. In this embodiment, proximal portion 912 of delivery device 900 includes hub 951. Hub 951 includes needle 917, inflation cannula 930 and guidewire cannula 935. A material for hub 951 is, for example, a polycarbonate or acrylonitride butadiene styrene (ABS). A distal end of hub 951 has an opening to accommodate a proximal end of primary cannula 910. Hub 951 also has a number of cavities at least partially therethrough (extending in a distal to proximal direction) to accommodate needle 917, inflation cannula 930 and guidewire cannula 935. A proximal portion of hub 951 flares to separate a spacing between needle 917, inflation cannula 930 and guidewire cannula 935. Similar hubs may be used in the other delivery devices described herein.

In one embodiment, hub 951 functions to control needle movement. As shown in FIG. 18, hub 951 includes cavity or channel 952 through which a portion of needle 917 may be disposed. In one embodiment, needle 917 has slider 957 attached to a portion thereof. Slider 957 is a protuberance (e.g., a plastic protuberance) that may be fixed to needle 917. Slider 957 is positioned on/around needle 917 within cavity 952 in hub 951 so that slider 957 is within cavity 952. Slider 957 limits the proximal and distal movement of needle 917 to a length, L, of cavity 952. A representative length, L, of cavity 952 is on the order of about 4.5 centimeters. Slider 957 also functions to limit the rotation of needle 917 within a lumen of needle cannula 915. In this manner, slider 957 is of a size such that it cannot be rotated within cavity 952.

Referring to distal portion 913 of delivery device 900, delivery device 900 is shown in a configuration where balloon 920 is expanded (inflated) and needle 917 extends from a distal end of needle cannula 915 into a wall of blood vessel 905 and into a periadventitial space.

In one embodiment, a treatment agent such as a cellular component, a small molecule drug, protein, peptide, or gene construct in solution or in suspension with a controlled release microsphere or liposome formulation may be introduced through port 9170 of needle 917 through a distal end of needle 917 into a periadventitial space. In this manner, the treatment agent, in one example, may migrate through the fatty layer and bathe the epicardium and coronary arteries. Due to the position of balloon 920 adjacent lesion 907, needle 917 is introduced into a wall of blood vessel 905 at a point proximal to lesion 907. In another embodiment, stent 925 may be deployed, followed by deflation of balloon 920, distal advancement of delivery device 900, inflation of balloon 920, and introduction of needle 917 at a point distal to lesion 907.

Figure 19:
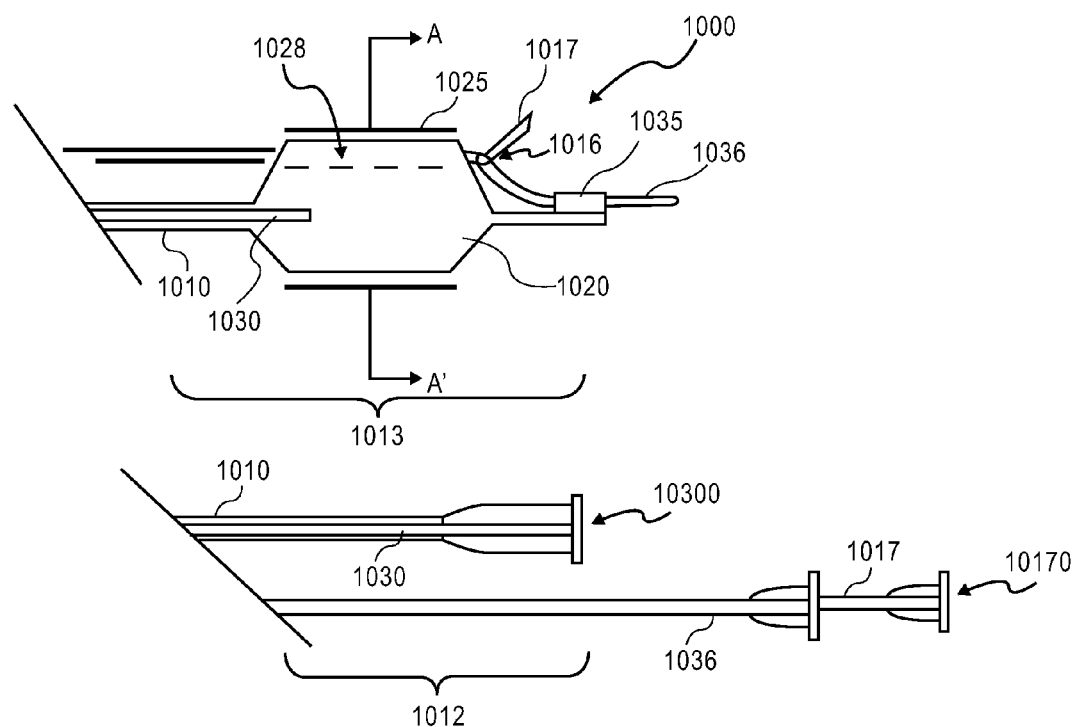
FIG. 19 shows a cross-sectional side view of another embodiment of a delivery device in a blood vessel capable of deploying a stent.

FIG. 19 shows another embodiment of a delivery device suitable for deploying a stent to treat a target lesion as well as introducing a treatment agent to address diffuse disease and/or less occlusive vulnerable plaques. Delivery device 1000 is a catheter device including proximal portion 1012 intending to be resident outside of a patient during a procedure and distal portion 1013 intended to be resident within a blood vessel of a patient during a procedure (e.g., resident in a coronary artery). Delivery device 1000 includes primary cannula 1010 extending from proximal portion 1012 to distal portion 1013. Primary cannula 1010 has a lumen therethrough. Disposed within a lumen of primary cannula 1010 is inflation cannula 1030 extending from a proximal end of delivery device 1000 (at port 10300) beyond a distal end of primary cannula 1010. Delivery device 1000 also includes balloon 1020 connected at a distal end of primary cannula 1010. Inflation cannula 1030 extends beyond a distal end of primary cannula 1010 into balloon 1020. In one embodiment, balloon 1020 may be expanded by introducing a fluid through a lumen of inflation cannula 1030.

Positioned on an exterior portion of balloon 1020 is stent 1025. Thus, balloon 1020 may be used, in one embodiment, to deliver and deploy stent 1025 in a blood vessel. FIG. 19 shows balloon 1020 in an expanded state, such as to deploy stent 1025.

Delivery device 1000 shown in FIG. 19 is a rapid exchange (RX) type catheter. Delivery device 1000 includes guidewire cannula 1035 located distal to balloon 1020. In an RX configuration, delivery device 1000 may be advanced over a guidewire where only the distal portion of the delivery device (the portion including guidewire cannula 1035) is advanced over the guidewire. FIG. 19 shows delivery device 1000 over guidewire 1036.

Referring to guidewire 1036 associated with delivery device 1000, in one embodiment, guidewire 1036 is hollow or defines a lumen therethrough through which a needle may be advanced. FIG. 19 shows guidewire 1036 having access port 1016 through which needle 1017 may exit guidewire 1036. In one embodiment, needle 1017 may be made of a shape memory material. In this manner, when needle 1017 is retracted (within a lumen of guidewire 1036), the needle is hidden and conforms to the shape of the lumen. Upon exiting access port 1016, needle 1017 returns to a memorized shape (e.g., a curved shape). A suitable shape memory material from which to form needle 1017 is a nickel-titanium alloy. FIG. 19 shows a portion of needle 1017 outside access port 1016. Needle 1017 is curved upward (as viewed) such that it may be advanced into a wall of a blood vessel. A treatment agent may be introduced through a lumen of needle 1017 at port 10170 at a proximal end of needle 1017.

Figure 20:
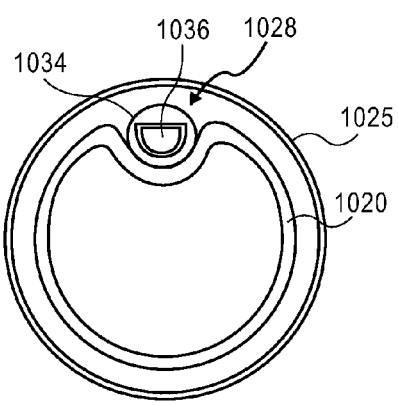
FIG. 20 shows a cross-sectional side view through line A-A' of FIG. 19.

FIG. 20 shows a side view through line A-A'. FIG. 20 shows balloon 1020 molded with longitudinal trench 1028 into which cannula tube 1034 is bonded. In one manner, balloon 1020 may be molded by using a mandrel having a shape to include the trench 1028 and forming balloon 1020 over the mandrel. A balloon of PEBAX™ polyurethane and silicone and SBC is suitable. Cannula 1034 may be a polymer material that may be bonded to an exterior surface of balloon 1020 in trench 1028 through an adhesive or heat. Cannula 1034 may extend an entire length of the medial working length of balloon 1020 or a distance less than the entire medial working length. In one embodiment, cannula 1034 provides for free guidewire movement under stent 1025 (see FIG. 19) and allows for uniform stent deployment when balloon 1020 is inflated. In other words, the diameter of balloon 1020 at trench 1020 plus the diameter of cannula 1034 equals the diameter of the other regions of balloon 1020. When balloon 1020 is inflated, Cannula 1034 enhance guidewire 1036 will be adjacent the blood vessel wall, permitting needle access to the blood vessel wall if port 1016 of guidewire 1036 is just proximal or distal to cannula 1034.

In one embodiment, to assure that needle port 1016 in guidewire 1036 is pointed towards a wall of the blood vessel, the rotation of guidewire 1036 is minimized such as by forming an exterior portion of guidewire 1036 and interior portion of cannula 1034 of a similar non-circular shape. For example, an interior of cannula 1034 that defines the lumen therethrough may be "D" shaped and guidewire 1036 may also have a portion that is "D" shape and of a size such that portion of guidewire 1036 containing the D shape will only pass through cannula 1034 if the shapes of the guidewire and the cannula lumen coincide.

Figure 21:
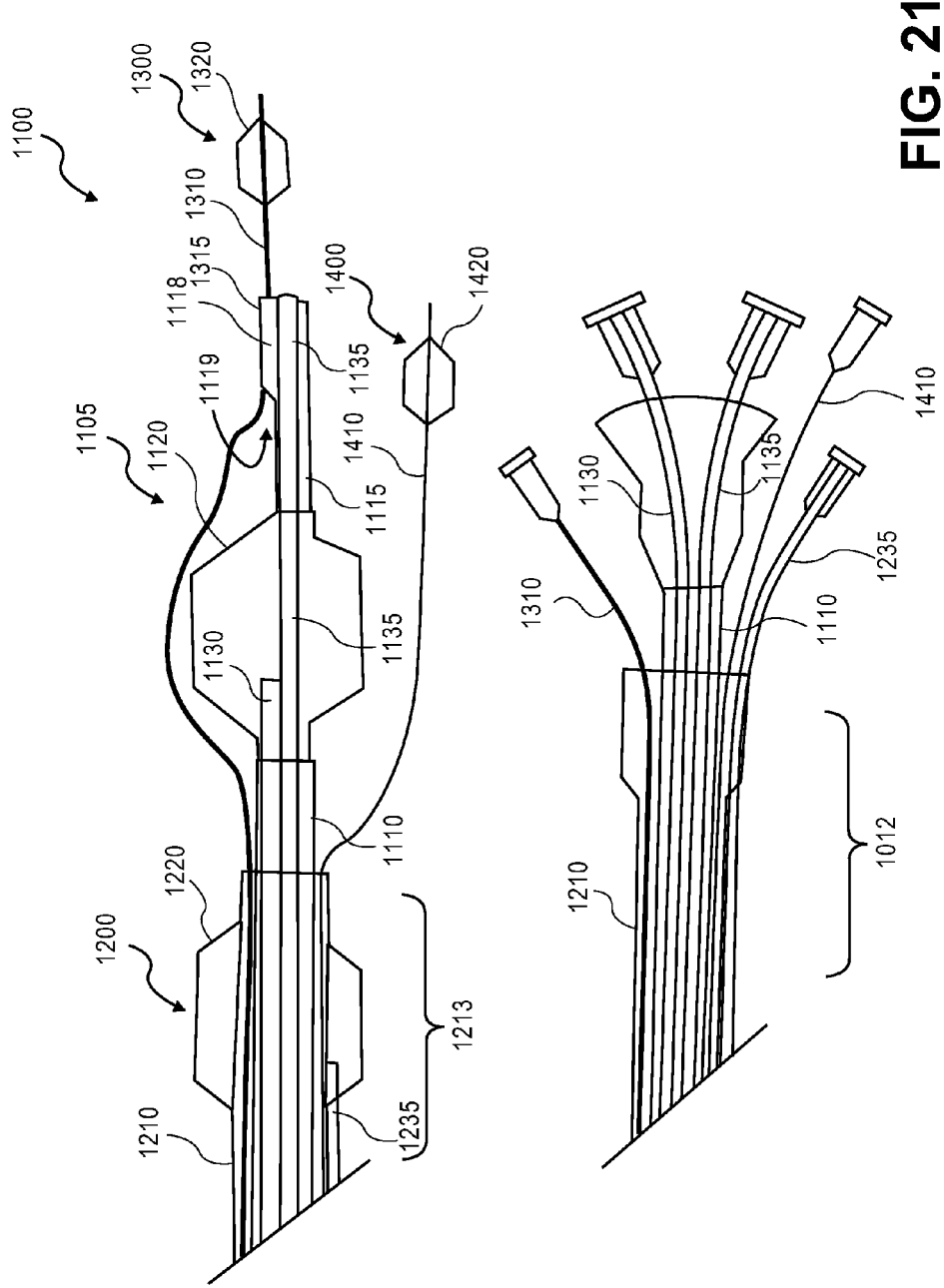
FIG. 21 shows a system suitable for retrograde infusion of a treatment agent.

FIG. 21 shows an embodiment of the delivery device that may be used in conjunction with a conventional stent delivery device similar, for example, to the device described with reference to FIG. 16 and the accompanying text. In particular, the delivery device shown in FIG. 21 and described below may be inserted through a venous route and treatment agent delivered in a retrograde fashion while the stent delivery device (e.g., device 700 in FIG. 16) is introduced in a conventional manner through an arterial route.

Referring to FIG. 21, system 1100 is includes a guide catheter, delivery catheter, and two guidewires, each component including an occlusion device. In one embodiment, system 1100 includes delivery catheter 1105, guide catheter 1200 and guidewire 1300 and guidewire 1400.

Guide catheter 1200 of system 1100 includes primary cannula 1210 having a lumen therethrough allowing guide catheter 1200 to be maneuvered over a guidewire, such as guidewire 1300. In one embodiment, the lumen of primary cannula 1210 of guide catheter 1200 extends the length of guide catheter 1200 from proximal portion 1212 to distal portion 1213. In use, proximal portion 1212 of guide catheter 1200 is intended to be resident outside a patient while distal portion 1213 is deployed in a blood vessel within a patient during a treatment. Representatively, in a procedure, guidewire 1300 may be initially advanced through a region of interest in a blood vessel and guide catheter 1200 is advanced on/over the guidewire to a desired position in an over-the-wire (OTW) fashion.

In the embodiment shown in FIG. 21, guide catheter 1200 includes occlusion device 1220. In one embodiment, occlusion device 1220 may be an inflatable balloon (i.e., balloon). In another embodiment, occlusion device 1220 may be a mechanical, cage-like structure such as described above with reference to FIGS. 4-15 and the corresponding text. As an inflatable balloon, occlusion device 1220 may be inflated with, for example, a fluid introduced through inflation cannula 1235. As a guide catheter, a lumen of primary cannula 1210 also serves as an opening through which a delivery catheter (delivery catheter 1105) may be advanced. Accordingly, inflation cannula 1235, in one embodiment, is disposed on an exterior of primary cannula 1210 as is balloon 1220 (i.e., balloon 1220 is attached to an exterior wall of primary cannula 1210).

System 1100 also includes delivery catheter 1105. Delivery catheter 1105 is shown disposed through a lumen of primary cannula 1210 of guide catheter 1200. Delivery catheter 1105 includes primary cannula 1110 that extends from a proximal end of delivery catheter 1105 to a distal portion. Primary cannula 1110 includes a lumen therethrough. Connected to a distal end of primary cannula 1110 is occlusion device 1120. In the embodiment shown, occlusion device 1120 is an inflatable balloon. In another embodiment, occlusion device 1120 may be a mechanical cage-like structure such as described with reference to FIGS. 4-15 and the accompanying text. In an embodiment where occlusion device 1120 is a balloon, delivery catheter 1105 includes inflation cannula 1130 that extends from a proximal end of delivery catheter 1105 into the balloon. At a distal end, the balloon is connected to secondary cannula 1115.

Delivery catheter 1105 of system 1100 also includes delivery cannula 1135 extending from a proximal end of the catheter through primary cannula 1110, through balloon 1120 and to secondary cannula 1115 to a distal end of delivery catheter 1105. A lumen of secondary cannula 1115 also includes guidewire cannula 1118 disposed with a length that is defined between a distal end of balloon 1120 and a distal end of delivery catheter 1105. In this manner, delivery catheter 1105 is a rapid exchange (RX) type catheter wherein only a distal portion of delivery catheter 1105 is fed over guidewire 1300 (with delivery catheter 1105 advanced over a guidewire at port 1119).

Catheter system 1100 also includes guidewire 1300 having an occlusion device. FIG. 21 shows guidewire 1300 including wire 1310 and occlusion device 1320 connected to wire 1310 at a distal portion. In one embodiment, occlusion device 1320 may be an inflatable balloon. In another embodiment, occlusion device 1320 may be a mechanical, cage-like structure similar to that described with reference to FIGS. 4-15 and the accompanying text. In an embodiment where occlusion device 1320 is an inflatable device, wire 1310 may define a lumen therethrough, such lumen terminating in occlusion device 1320. An example of a guidewire with a balloon as an occlusion device is a PERCUSURE™ guidewire, commercially available from Medtronic, Inc. of Minneapolis, Minn.

System 1100 also includes guidewire 1400. FIG. 21 shows guidewire 1400 including wire 1410 and occlusion device 1420 connected to wire 1410 at a distal portion. Similar to occlusion device 1320, occlusion device 1420 may be a mechanical cage-like structure or an inflatable balloon. FIG. 21 shows guide catheter 1200 advanced over each of guidewire 1300 and guidewire 1400. The occlusion device of each guidewire extends distally beyond guide catheter 1200 (and occlusion device 1320 of guidewire 1300 extends distally beyond a distal end of delivery catheter 1105).

As noted above, in one embodiment, catheter system 1100 may be used in conjunction with a stent delivery device, where, for example, the stent delivery device is positioned in a coronary artery to treat a target lesion while catheter system 1100 is inserted through a venous route to deliver a treatment agent to capillaries and arterioles distal to the target lesion that may suffer diffuse disease or injury as a result of the target lesion. Representatively, guide catheter 1200 of catheter system 1100 is inserted in a femoral vein and a coronary sinus of a patient is accessed with the guide catheter through the inferior veno cava or the superior veno cava.

Figure 22:
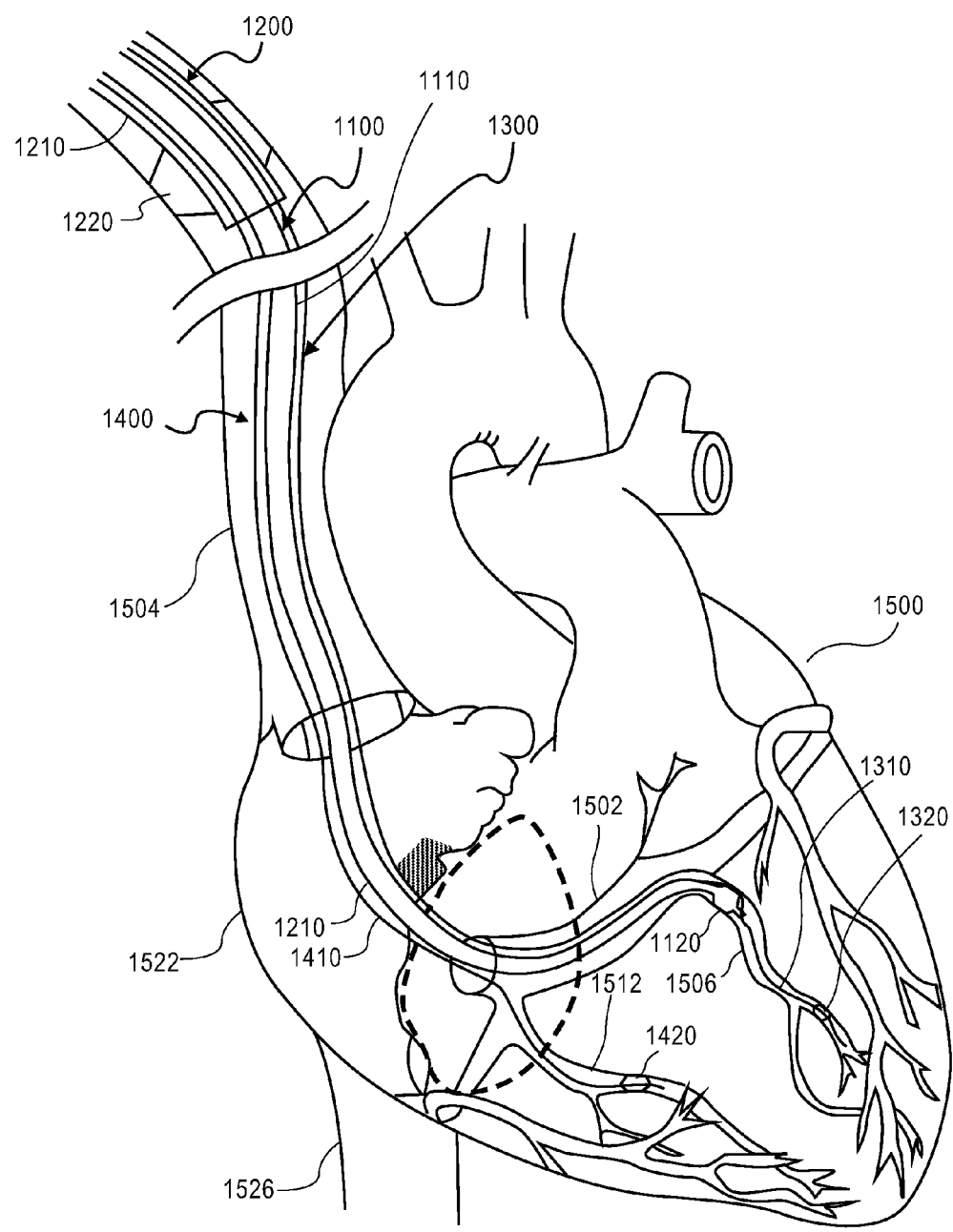
FIG. 22 shows a perspective side view of a human heart with the device of FIG. 21 shown therein.

FIG. 22 schematically illustrates the placement of catheter system 1100 of FIG. 21 in a coronary sinus of a patient. FIG. 22 shows guidewire 1300, delivery catheter 1105 and guidewire 1400 extending through superior veno cava 1504. Delivery catheter 1105 may be fed through a lumen of primary cannula 1210 of guide catheter 1200 and into middle cardiac vein 1506. Guidewire 1320 may have been previously routed to middle cardiac vein 1506 thus allowing delivery catheter 1105 to be advanced to the location.

As shown in FIG. 22, occlusion device 1320 of guidewire 1300 is located at a position distal from a distal end of delivery catheter 1105. FIG. 22 also guidewire 1400 may be fed into small cardiac vein 1312.

Following the positioning of each guidewire 1300, delivery catheter 1105 and guidewire 1400, occlusion device 1320, occlusion device 1120, and occlusion device 1420 are expanded to occlude small cardiac vein 1512 and respectively occlude a portion of middle cardiac vein 1506 between balloon 1120 and occlusion device 1320. Occlusion device 1420 is expanded to occlude small cardiac vein 1512 to inhibit any treatment agent dispensed through delivery catheter 1105 from reaching the right atrium of heart 1500 through shunts anastimoses.

In one embodiment, following the deployment of catheter system 1100 including the engagement of the individual occlusion devices, a pressurized perfusion of a treatment agent may be delivered through delivery cannula 1135 of delivery catheter 1105. The pressurized delivery will drive the solution or suspension into the capillaries, and the capillaries associated with the relevant artery, and then into the arterioles for treatment. Devices and techniques for pressurized delivery in a retrograde fashion are described in commonly-owned U.S. patent application Ser. No. 10/387,048 titled, "Retrograde Pressure Regulating Diffusion," filed Mar. 12, 2003, and U.S. patent application Ser. No. 10/800,323 titled, "Infusion Treatment Agents, Catheters, Filter Devices, and Occlusion Devices, and Use Thereof," filed Mar. 11, 2004.

With respect to the embodiments described in FIGS. 16-22, a concurrent and combination of therapy is achieved by deploying a conventional stent or a drug eluting stent at a target lesion site and a treatment agent delivered to circulate downstream and transport transluminally to periadventitial state. In one embodiment, the treatment agent is a microparticle and/or nanoparticle solution or suspension that may potentially accompany direct infusion of the same or another treatment agent dissolved or suspended in a carrier fluid. The nanoparticles and the carrier fluid together may be termed and infusate. The infusate parameters optimized include a mix population of multiple types of treatment agents within the microparticles and/or nanoparticles, the size and distribution of the particles, the bulk properties of the particles, the surface chemistry of the particles, host material response property of the particles and the carrier, and the rheological properties of the carrier.

Concurrent and combination therapy such as described potentially provides multiple options to treat coronary artery disease in general based on a treatment agent selection, treatment agent combinations, and vascular access. For example, complete bathing of the coronary vasculatures possible by retrograde perfusion or via access to the pericardial sac of a patient. The concurrent and combination therapy may also provide the option for point-of-care selection of an infusate to be commensurate with a patient population and decided by an interventional cardiologist. Combination therapy may lead to bioactive distribution transluminally into adventitial space, distally in the target vessel and also in the side braches of bifurcation lesions.

In the preceding detailed description, reference is made to specific embodiments thereof. It will, however, be evident that various modifications and changes may be made thereto without departing from the broader spirit and scope of the following claims. The specification and drawings are, accordingly, to be regarded in an illustrative rather than a restrictive sense.

What is claimed is:

1. A method comprising:
   percutaneously positioning a delivery device in a coronary artery; and
   performing at least one cycle of injection and occlusion, wherein a single cycle of injection and occlusion comprises:
   locally introducing a treatment agent from the delivery device into the coronary artery upstream of at least one of an infarcted area or a distressed area, wherein introducing the treatment agent begins during a low flow time of a blood flow in the coronary artery, wherein the low flow time corresponds to a portion of the cardiac cycle including a period between a QRS complex of the cardiac cycle and a beginning of ventricular relaxation of the cardiac cycle, wherein the treatment agent is introduced at a first volumetric rate during the low flow time of the blood flow in the coronary artery and at a second volumetric rate during a high flow time of the blood flow in the coronary artery, and wherein the first volumetric rate is higher than the second volumetric rate, and
   occluding the coronary artery, after locally introducing the treatment agent during the low flow time and the high flow time, to stop the blood flow in the coronary artery, wherein the coronary artery is occluded for a dwell time to allow the treatment agent to flow into targeted capillaries that are at least one of in or adjacent to the at least one of the infarcted area or the distressed area.

2. The method of claim 1, wherein locally introducing the treatment agent comprises introducing an amount of the treatment agent to fill the coronary artery that feeds the targeted capillaries and under a condition that minimizes an increase in ischemia of healthy tissues fed by arterioles and capillaries distal to a point of the introduction of the treatment agent, wherein the first volumetric rate displaces a majority of the blood flow at the infarcted area or the distressed area in the coronary artery without causing the treatment agent to flow upstream, and wherein the second volumetric rate does not cause a pressure in the coronary artery to raise above a predetermined threshold.

3. The method of claim 2, wherein the amount of the treatment agent to fill the coronary artery that feeds the targeted capillaries is determined based on at least two of the following:
   a size of the coronary artery at a point of introduction;
   a weight of a patient receiving the treatment agent; or
   an externally measured blood flow parameter.

4. The method of claim 1 further comprising:
   locally introducing a contrast agent from the delivery device into the coronary artery upstream of the infarcted area or the distressed area in the coronary artery, wherein introducing the contrast agent begins during a prior cardiac cycle before the cardiac cycle; and
   determining a volume of the contrast agent, wherein the volume of the contrast agent fills the infarcted area or the distressed area, and wherein the volume corresponds to the first volumetric flow rate to introduce the treatment agent.

5. The method of claim 1, wherein occluding the coronary artery continues for a time after introducing the treatment agent such that the treatment agent flows into the targeted capillaries and comprises, prior to introducing the treatment agent:
   locally introducing a contrast agent into the coronary artery; and
   determining a delay time to occlude the coronary artery after introducing the treatment agent, wherein the delay time includes a time it takes to fill the targeted capillaries with the contrast agent.

6. The method of claim 1, wherein the low flow time of the blood flow in the coronary artery includes a point of time following a contraction of the ventricles of a patient receiving the treatment agent.

7. The method of claim 1, wherein the low flow time of the blood flow in the coronary artery includes a point of time between an S wave and a T wave of an electrocardiogram for a patient receiving the treatment agent.

8. The method of claim 7, wherein introducing the treatment agent at the first volumetric rate is completed prior to a start of a subsequent P wave of the electrocardiogram.

9. The method of claim 1, wherein occluding the coronary artery comprises expanding an occluding portion of the delivery device without inflating.

10. The method of claim 9, wherein the occluding portion of the delivery device is self-expanding.

11. The method of claim 10, wherein the delivery device comprises an occluding portion and a longitudinally movable sheath having a lumen therethrough, the method comprising:
  positioning the delivery device in the coronary artery with the sheath over the occluding portion; and
  retracting the sheath, after introducing the treatment agent, to expose the occluding portion.

12. A system comprising:
  a delivery device suitable for percutaneous insertion into a coronary artery of a patient, the delivery device comprising an occluding portion and a delivery cannula having a lumen therethrough; and
  a controller coupled to a proximal portion of the delivery device comprising instruction logic to perform a method comprising:
  performing at least one cycle of injection and occlusion, wherein a single cycle of injection and occlusion comprises:
    locally introducing a treatment agent from the delivery device into the coronary artery upstream of at least one of an infarcted area or a distressed area, wherein introducing the treatment agent begins during a low flow time of a blood flow in the coronary artery, wherein the low flow time corresponds to a portion of the cardiac cycle including a period between a QRS complex of the cardiac cycle and a beginning of ventricular relaxation of the cardiac cycle, wherein the treatment agent is introduced at a first volumetric rate during the low flow time of the blood flow in the coronary artery and at a second volumetric rate during a high flow time of the blood flow in the coronary artery, and wherein the first volumetric rate is higher than the second volumetric rate, and
    occluding the coronary artery, after locally introducing the treatment agent during the low flow time and the high flow time, to stop the blood flow in the coronary artery, wherein the coronary artery is occluded for a dwell time to allow the treatment agent to flow into targeted capillaries that are at least one of in or adjacent to the at least one of the infarcted area or the distressed area.

13. The system of claim 12, wherein occluding the coronary artery continues for the time after introducing the treatment agent such that the treatment agent flows into the targeted capillaries, wherein the targeted capillaries are at least one of in or adjacent to an infarcted area and a distressed area, and the method performed by instruction logic of the controller further comprising:
  prior to introducing the treatment agent, locally introducing a contrast agent into the coronary artery; and
  determining a time it takes to visualize the contrast agent in the targeted capillaries.

14. The system of claim 12, wherein the controller may receive cardiac sensor information, and the controller further comprises instruction logic to perform a method comprising identifying the low flow portion of the cardiac cycle including the period between the QRS complex of the cardiac cycle and the beginning of ventricular relaxation of the cardiac cycle.

15. The system of claim 12, wherein the first volumetric rate displaces a majority of the blood flow at the infarcted area or the distressed area in the coronary artery without causing the treatment agent to flow upstream, and wherein the second volumetric rate does not cause a pressure in the coronary artery to raise above a predetermined threshold.

* * * * *